United States Patent
Kim

(10) Patent No.: US 11,666,608 B2
(45) Date of Patent: Jun. 6, 2023

(54) **COMPOSITION FOR PREVENTION OR TREATMENT OF OCULAR DISEASES COMPRISING EXTRACELLULAR VESICLES DERIVED FROM *MICROCOCCUS LUTEUS***

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 17/646,140

(22) Filed: Dec. 27, 2021

(65) Prior Publication Data

US 2022/0202877 A1   Jun. 30, 2022

(30) Foreign Application Priority Data

Dec. 28, 2020 (KR) .................. 10-2020-0184337
Oct. 18, 2021 (KR) .................. 10-2021-0138713

(51) Int. Cl.
*A61K 35/74*     (2015.01)
*A61P 27/02*    (2006.01)
*A61K 9/127*    (2006.01)

(52) U.S. Cl.
CPC .............. *A61K 35/74* (2013.01); *A61K 9/127* (2013.01); *A61P 27/02* (2018.01)

(58) Field of Classification Search
None
See application file for complete search history.

(56) References Cited

U.S. PATENT DOCUMENTS

| 10,888,591 | B2 * | 1/2021 | Kim | ............... | A23L 33/135 |
| 2015/0132366 | A1 | 5/2015 | Benedetti | | |
| 2018/0008629 | A1 * | 1/2018 | Dixit | ............... | A61K 9/1271 |

FOREIGN PATENT DOCUMENTS

| EP | 3441069 A1 * | 2/2019 | ........... A61K 31/496 |
| KR | 10-2016-0073157 A | 6/2016 | |
| KR | 10-1830058 B1 | 2/2018 | |
| KR | 10-2019-0103962 A | 9/2019 | |

OTHER PUBLICATIONS

Yerramothu et al (Eye, 2018, 32, 491-505) (Year: 2018).*
Mead et al., "Extracellular vesicle therapy for retinal diseases", Progress in Retinal and Eye Research, 2020, vol. 79, p. 100849, 15 pages.

* cited by examiner

*Primary Examiner* — Celeste A Roney
(74) *Attorney, Agent, or Firm* — Vorys, Sater, Seymour and Pease LLP; Mih Suhn Koh

(57) ABSTRACT

Provided is a method for preventing, alleviating or treating an ocular disease including administering a composition containing vesicles derived from *Micrococcus luteus* as an active ingredient wherein the vesicles are delivered to the central nervous system including the retina through the blood-brain barrier (BBB); when epithelial cells and macrophages were treated with the vesicles, not only is the secretion of an inflammatory mediator by a biological causative factor considerably inhibited, but also NLRP3 protein expression by a biological causative factor is inhibited; and when the vesicles are administered to a rabbit model with an ocular disease caused by oxidative stress, retinal degeneration is significantly inhibited, thus the vesicles derived from *Micrococcus luteus* can be used for a composition for preventing, alleviating or treating an age-related ocular disease and an inflammatory ocular disease, including a pharmaceutical or health functional food composition.

15 Claims, 33 Drawing Sheets

COMPOSITION FOR PREVENTION OR TREATMENT OF OCULAR DISEASES COMPRISING EXTRACELLULAR VESICLES DERIVED FROM *MICROCOCCUS LUTEUS*

TECHNICAL FIELD

The present invention relates to extracellular vesicles derived from *Micrococcus luteus* and a use thereof, and more particularly, to a composition for preventing or treating an ocular disease, which comprises extracellular vesicles derived from *Micrococcus luteus* as an active ingredient.

This application claims priority to and the benefit of Korean Patent Application Nos. 10-2020-0184337 and 10-2021-0138713 filed in the Korean Intellectual Property Office on Dec. 28, 2020 and Oct. 18, 2021, respectively, and all the contents disclosed in the specification and drawings of the applications are incorporated in this application.

BACKGROUND ART

Since the beginning of the 21st century, acute infectious diseases recognized as epidemic diseases in the past have become less important, whereas chronic diseases accompanied by immune dysfunction caused by disharmony between humans and symbiotic microorganism and age-related chronic diseases that occur in major organs of our body have changed disease patterns as main diseases that determine the quality of life and human lifespan. As $21^{st}$ century intractable chronic diseases characterized by abnormalities in immune and metabolic functions caused by various stresses, cancer, cardiovascular diseases, chronic lung diseases, metabolic diseases, and neuro-psychiatric diseases are major diseases determining human lifespans and quality of life and becoming a big problem in public health.

Aging refers to the deterioration in organ function in the body over time, and the accumulation of cellular damage over time is believed to be a common cause of aging. It was revealed that an NLRP3 inflammasome activated in response to various damage-associated molecular patterns (DAMPs) that increase with age, such as extracellular ATP, hyperglycemia, ceramides, amyloids, uric acid crystals, cholesterol crystals, etc., is particularly deeply related to aging. Accordingly, the NLRP3 inflammasome has become a target for prevention and treatment of an age-related disease, and since an age-related chronic disease may be characterized by chronic inflammation accompanying abnormalities of immune and metabolic functions and cell death, it has been reported that aging-related diseases can be inhibited by inhibiting NLRP3 inflammasome-associated inflammation.

Immunity is a cellular defense mechanism against biological, chemical, physical and mental stress, and occurs through innate immunity and adaptive immunity. Recently, relative to the etiology of an inflammatory disease, a pathogen-associated molecular pattern (PAMP) derived from a biological causative factor and a damage-associated molecular pattern (DAMP), which is a danger signal generated by cell damage, are recognized by nucleotide-binding oligomerization domains (NLRPs) which are pattern recognition receptors, and among these, the fact that NLRP3 forms an NLRP3 inflammasome, and causes various intractable diseases is attracting attention.

Metabolism is to make energy required for the body to produce various materials performing cell functions, and provides proteins and lipids, which have been produced in the endoplasmic reticulum (ER) by ATP produced in mitochondria, to a region in need thereof. Cells face various stresses from the moment cells are generated, and biological, chemical, physical and psychological stress induces ER stress, mitochondrial dysfunction, and lysosomal damage in cells and activate the NLRP3 inflammasome to induce cell death, leading to various diseases.

Meanwhile, the retina of the eye is an organ belonging to the central nervous system, and mature retinal cells do not divide under normal conditions like most of neuronal cells present in brain. Accordingly, when the function of retinal cells decreases, it is easy to have abnormalities in visual function, and aging rapidly progresses. The biggest cause of deteriorated retinal cell function is oxidative stress, which is because tissues for constituting the eye, including the retina, optic nerve, photoreceptor cells and lens, are constantly exposed to oxidative stress such as light and UV in daily life. Due to such oxidative stress, as the alteration of DNA, proteins and lipids constituting a cell occurs and cell death is induced, ocular aging occurs, and seriously, age-related ocular diseases such as retinal geographic atrophy, diabetic retinopathy, cataracts, glaucoma, xerophthalmia, and the like occur.

In addition, when vision-related cells do not properly defend against environmental stress such as blue light and UV, inflammation of eyes occurs, and chronic inflammatory ocular disease occurs due to repeated stress. Recently, in order to treat or prevent these chronic inflammatory ocular diseases, interest in an inhibitor of an inflammatory cytokine, TNF-α, which is known as a major mediator of an inflammatory disease, is increasing.

It is known that the number of microorganisms that coexist in the human body reaches 100 trillion, which is about 10-fold larger than that of human cells, and the number of genes of microorganisms is 100-fold larger than that of humans. A microbiota or microbiome refers to a microbial community including bacteria, archaea and eukarya present in a given habitat.

Bacteria that coexist in our bodies and bacteria that exist in the surrounding environment secrete nanometer-sized vesicles to exchange information such as genes, low molecular compounds, and proteins with other cells. The mucosa forms a physical defense membrane through which particles having a size of 200 nanometers (nm) or more cannot pass, so that bacteria coexisting in the mucosa cannot pass through the mucosa, but bacteria-derived vesicles have a size of 200 nanometers or less, and thus relatively freely pass through epithelial cells via the mucosa to be absorbed in our bodies. As described above, although bacteria-derived vesicles are secreted from bacteria, they differ from bacteria in terms of their constituents, absorption rate in the body, and risk of side effects, and therefore, the use of bacteria-derived vesicles is completely different from that of living cells or has a significant effect.

Locally secreted bacteria-derived vesicles are absorbed through the epithelial cells of the mucosa to induce a local inflammatory response, and vesicles that have passed through the epithelial cells are systemically absorbed through a lymphatic vessel to be distributed to respective organs, and regulate immune and inflammatory responses in the distributed organs. For example, extracellular vesicles derived from pathogenic gram-negative bacteria such as *Escherichia coli* (*E. coli*) are pathogenic nanoparticles mimicking viruses and locally cause colitis, and when absorbed into blood vessels, promote systemic inflammatory responses and blood coagulation through vascular endothelial inflammatory responses, and are absorbed into myocytes on which insulin acts, causing insulin resistance and diabetes. On the other hand, vesicles derived from beneficial bacteria may control diseases by regulating abnormalities in immune and metabolic functions caused by pathogenic vesicles.

*Micrococcus luteus* refers to gram-positive bacteria belonging to the genus *Micrococcus*, which is widely distributed in nature, such as water, dust, and soil. These bacteria are known to produce riboflavin when grown in toxic organic pollutants such as pyridine, and absorb UV light by the lutein pigment. These bacteria are also known to be isolated from dairy products and beer, grown in a dry environment or high-salt environment, and survive for a long time at a refrigeration temperature, for example in a refrigerator, although not forming spores.

However, no case of application to the treatment of an ocular disease using *Micrococcus luteus*-derived vesicles has been reported.

DISCLOSURE

Technical Problem

The inventors have earnestly studied to solve the conventional problems, confirming that, when cells were treated with vesicles derived from *Micrococcus luteus*, the vesicles not only significantly inhibit the secretion of an inflammatory mediator by pathogenic nanoparticles, but also efficiently inhibit abnormal immune function by a biological pathogenic factor. In addition, it was confirmed that the vesicles derived from *Micrococcus luteus* inhibit the expression of an NLRP3 protein, which is a pattern recognition receptor associated with causes of various diseases, and abnormal immune function by increasing endothelial NO synthase (eNOS) signaling. In addition, it was confirmed that, when orally administered, the vesicles are delivered to the central nervous system through the blood brain barrier (BBB). Further, when a rabbit model with an ocular disease caused by oxidative stress was treated with the vesicles, it was confirmed that retinal degeneration is inhibited in a dose-dependent manner. Thus, the present invention was completed.

Thus, an object of the present invention is to provide a pharmaceutical composition for preventing or treating an ocular disease, comprising vesicles derived from *Micrococcus luteus* as an active ingredient.

In addition, another object of the present invention is to provide a food composition for preventing or alleviating an ocular disease, comprising vesicles derived from *Micrococcus luteus* as an active ingredient.

In addition, another object of the present invention is to provide a quasi-drug composition for preventing or alleviating an ocular disease, comprising vesicles derived from *Micrococcus luteus* as an active ingredient.

In addition, another object of the present invention is to provide an inhalant composition for preventing or alleviating an ocular disease, comprising vesicles derived from *Micrococcus luteus* as an active ingredient.

In addition, another object of the present invention is to provide a composition for delivering a drug for treating an ocular disease, comprising vesicles derived from *Micrococcus luteus* as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a pharmaceutical composition for preventing or treating an ocular disease, comprising vesicles derived from *Micrococcus luteus* as an active ingredient.

In addition, the present invention provides a food composition for preventing or alleviating an ocular disease, comprising vesicles derived from *Micrococcus luteus* as an active ingredient.

In addition, the present invention provides a quasi-drug composition for preventing or alleviating an ocular disease, comprising vesicles derived from *Micrococcus luteus* as an active ingredient.

In addition, the present invention provides an inhalant composition for preventing or alleviating an ocular disease, comprising vesicles derived from *Micrococcus luteus* as an active ingredient.

In addition, the present invention provides a composition for delivering a drug for treating an ocular disease, comprising vesicles derived from *Micrococcus luteus* as an active ingredient.

As an exemplary embodiment of the present invention, the ocular disease may be an ocular disease mediated by an NOD-like receptor pyrin domain-containing protein 3 (NLRP3) inflammasome, but the present invention is not limited thereto.

As another exemplary embodiment of the present invention, the ocular disease may be an age-related ocular disease, and specifically, the ocular disease may be one or more diseases selected from the group consisting of retinal geographic atrophy, diabetic retinopathy, cataracts, glaucoma, and xerophthalmia, but the present invention is not limited thereto.

As another exemplary embodiment of the present invention, the ocular disease may be an inflammatory ocular disease, and specifically, the ocular disease may be one or more diseases selected from the group consisting of conjunctivitis, scleritis, keratitis, iritis, uveitis, chorioretinitis, choroiditis, and retinitis, but the present invention is not limited thereto.

As another exemplary embodiment of the present invention, the vesicles may have an average diameter of 10 to 200 nm, but the present invention is not limited thereto.

As another exemplary embodiment of the present invention, the vesicles may be naturally secreted or artificially produced from *Micrococcus luteus*, but the present invention is not limited thereto.

As another exemplary embodiment of the present invention, the composition may inhibit the activity of an NOD-like receptor pyrin domain-containing protein 3 (NLRP3) inflammasome, but the present invention is not limited thereto.

As another exemplary embodiment of the present invention, the ocular disease may be one or more diseases selected from the group consisting of retinal geographic atrophy, diabetic retinopathy, cataracts, glaucoma, xerophthalmia, conjunctivitis, scleritis, keratitis, iritis, uveitis, chorioretinitis, choroiditis, and retinitis, but the present invention is not limited thereto.

In addition, the present invention provides a method for preventing or treating an ocular disease, the method comprising administering a composition comprising vesicles derived from *Micrococcus luteus* as an active ingredient to a subject in need thereof.

In addition, the present invention provides a use of a composition comprising vesicles derived from *Micrococcus luteus* as an active ingredient for preventing or treating an ocular disease.

In addition, the present invention provides a use of vesicles derived from *Micrococcus luteus* for preparing a drug for preventing or treating an ocular disease.

In addition, the present invention provides a method of delivering a drug for treating an ocular disease, the method comprising administering a composition comprising vesicles derived from *Micrococcus luteus* containing a drug for treating an ocular disease as an active ingredient to a subject in need thereof.

In addition, the present invention provides a use of a composition comprising vesicles derived from *Micrococcus luteus* as an active ingredient for delivering a drug for treating an ocular disease.

In addition, the present invention provides a use of vesicles derived from *Micrococcus luteus* for preparing a drug for delivering a drug for treating an ocular disease.

Advantageous Effects

The inventors confirmed that, when vesicles derived from *Micrococcus luteus* were orally administered, the vesicles were delivered to the central nervous system through the blood brain barrier (BBB). In addition, it was confirmed that, when epithelial cells and macrophages were treated with the vesicles, not only is the secretion of an inflammatory mediator by a biological causative factor considerably inhibited, but also NLRP3 protein expression by a biological causative factor is inhibited. Further, it was confirmed that, when the vesicles are administered to a rabbit model with an ocular disease caused by oxidative stress, retinal degeneration caused by oxidative stress is significantly inhibited. Thus, it is expected that the vesicles derived from *Micrococcus luteus* according to the present invention can be effectively used for not only a composition for preventing, alleviating or treating an ocular disease, but also a drug delivery system for treating an ocular disease.

DESCRIPTION OF DRAWINGS

FIG. 4A shows an effect of inhibiting IL-8 secretion according to a concentration of *Micrococcus luteus*-derived vesicles; and FIG. 4B shows a comparison with the IL-8 secretion inhibitory effect of a positive control drug, dexamethasone (*P<0.05, P<0.01, *P<0.001, and hereinafter, n.s. indicates insignificant).

FIG. 6A shows an inhibitory effect on TNF-$\alpha$ secretion; and FIG. 6B shows an inhibitory effect on IL-6 secretion.

FIG. 10A shows a result of confirming the numbers of macrophages and neutrophils in bronchoalveolar lavage fluid (BALF) of mouse models; and FIG. 10B shows inflammatory cell infiltration in lung tissue in mouse models.

FIG. 11A is a result of measuring CXCL-1 secretion in bronchoalveolar lavage fluid (BALF); FIG. 11B is a result of measuring TNF-$\alpha$ secretion in bronchoalveolar lavage fluid (BALF); and FIG. 11C is a result of measuring IL-1$\beta$ secretion.

FIG. 12A is a result obtained by measuring IL-6 secretion; FIG. 12B is a result obtained by measuring IL-17 secretion; and FIG. 12C is a result obtained by measuring IL-10 secretion.

FIG. 15A is a result obtained by measuring the total number of inflammatory cells in bronchoalveolar lavage fluid (BALF); FIG. 15B is a result of measuring the number of neutrophils in bronchoalveolar lavage fluid (BALF); and FIG. 15C shows infiltration of inflammatory cells in lung tissue.

FIG. 16A is a result obtained by measuring an IL-1β concentration; and FIG. 16B is a result obtained by measuring an IL-17 concentration, which is a Th17 immune response indicator.

FIG. 18A shows a result of confirming eNOS signaling activity; and FIG. 18B shows a result of confirming iNOS signaling activity.

BEST MODE

Figure 1:
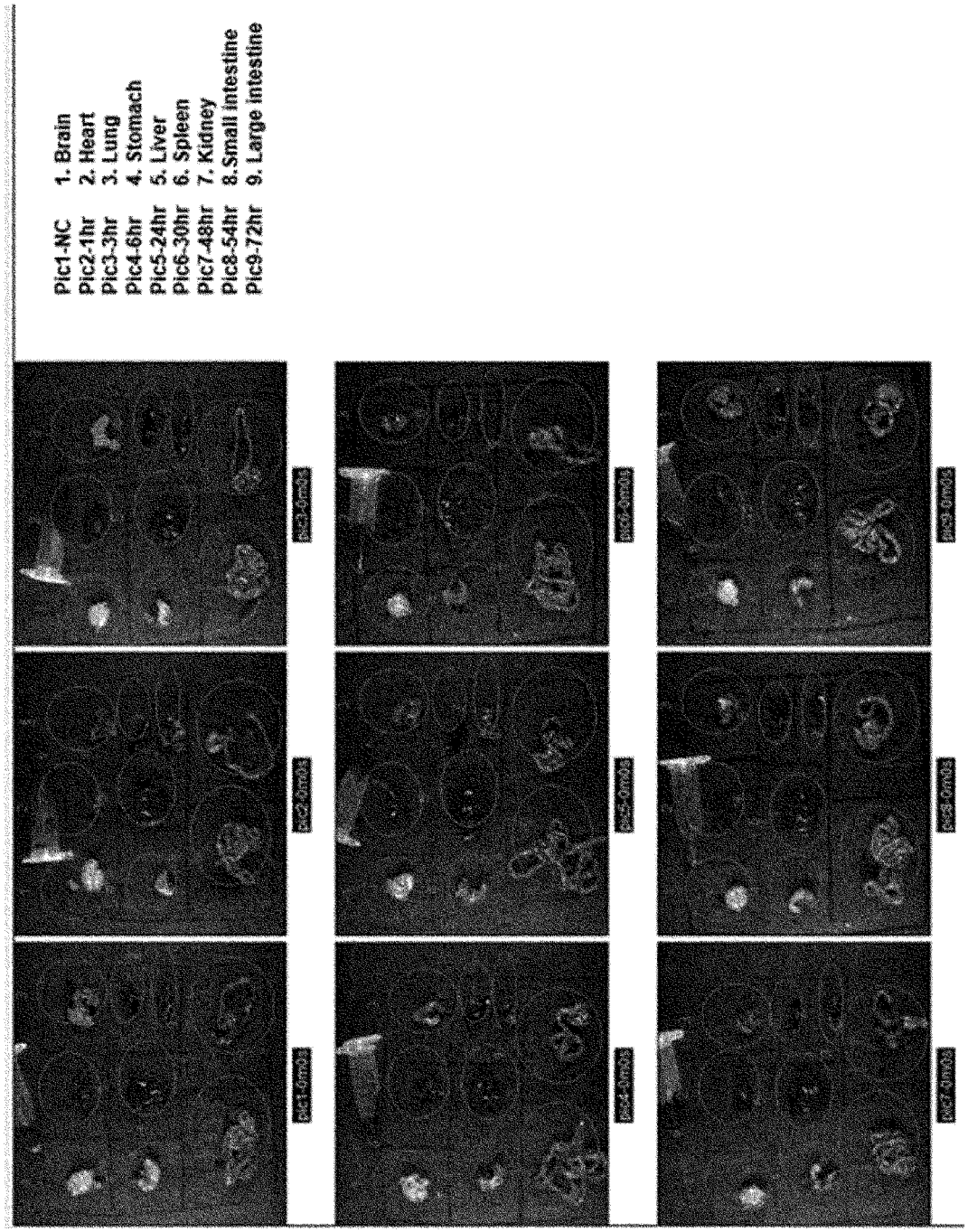
FIG. 1 shows a result of measuring fluorescence intensity in each organ by removing the organ over time after *Micrococcus luteus*-derived vesicles are orally administered to mice.

The present invention relates to vesicles derived from *Micrococcus luteus* and a use thereof.

The inventors confirmed that, when orally administered to mice, vesicles derived from *Micrococcus luteus* are absorbed into the entire body through mucosal membranes, and particularly distributed in brain tissue. In addition, they confirmed that, when epithelial cells are treated with the vesicles, they significantly inhibit secretion of an inflammatory mediator by pathogenic nanoparticles and are activated by endothelial NO synthase (eNOS) signaling, which occurs by inhibiting inducible NO synthase (iNOS) expression. In addition, it was confirmed that, when representative inflammatory cells, such as macrophages and neutrophils are treated with the vesicles, they can inhibit the secretion of inflammatory mediators caused by pathogenic nanoparticles and neutrophil activation in a dose-dependent manner, and when a mouse model with an inflammatory disease caused by pathogenic nanoparticles is administered the vesicles, inflammation caused by pathogenic nanoparticles is significantly inhibited. In addition, it was confirmed that, when a mouse model with an immune disease caused by a protein contaminated by LPS was treated with the vesicles, inflammation caused by a pathogen-associated molecular pattern (PAMP) is significantly inhibited, resulting in regulation of abnormal immune function. Based on this, the vesicles derived from *Micrococcus luteus* according to the present invention can be effectively used for a composition for preventing, improving or treating an age-related ocular disease and an inflammatory ocular disease.

Hereinafter, the present invention will be described in detail.

The inventors confirmed that, when the vesicles derived from *Micrococcus luteus* are orally administered to a mouse, the vesicles are distributed in brain tissue, the vesicles are delivered to the central nervous system including the retina through the blood brain barrier (BBB). In addition, it was confirmed that, when epithelial cells are treated with the vesicles, secretion of an inflammatory mediator by a biological causative factor is significantly inhibited, and when representative inflammatory cells, such as macrophages, and neutrophils are treated with the vesicles, secretion of an inflammatory mediator by a biological causative factor and neutrophil activation are inhibited in a dose independent manner. Further, it was confirmed that, when the vesicles are administered, NLRP3 protein expression in tissue by a biological causative factor is significantly inhibited, and when the vesicles are administered, endothelial NO synthase (eNOS) signaling inhibited by a biological causative factor is significantly restored. In addition, it was confirmed that, when the vesicles are administered to a rabbit model with an ocular disease caused by oxidative stress, the vesicles significantly inhibited retinal degeneration in a dose-dependent manner. Based on the above results, the present invention was completed.

Thus, the present invention provides a pharmaceutical composition for preventing or treating an ocular disease, comprising vesicles derived from *Micrococcus luteus* as an active ingredient.

The term "ocular disease" used herein refers to an eye-related disease, and in the present invention, the ocular disease may be an age-related or inflammatory ocular disease, and specifically, an ocular disease mediated by an NOD-like receptor pyrin domain-containing protein 3 (NLRP3) inflammasome or an ocular disease caused by oxidative stress, but the present invention is not limited thereto.

The term "age-related ocular disease" used herein is a concept that includes not only an ocular disease caused by degradation of biological functions with aging, but also an ocular disease exhibiting similar symptoms to those of a disease mainly occurring in the elderly due to degradation of biological functions faster than an actual age. The age-related ocular disease may include, for example, retinal geographic atrophy, diabetic retinopathy (DR), glaucoma, cataracts, xerophthalmia, and the like, but the present invention is not limited thereto.

The "retinal geographic atrophy" used herein is a disease in which the retina and choriocapillaris atrophy due to calcification of drusen, which are waste accumulating in the retinal pigment epithelium, due to the function decrease of eyes by aging and poor blood supply, and the atrophied area enlarges in a map shape and spreads to the central region, resulting in loss of vision.

The term "inflammatory ocular disease" used herein is a concept including all ocular diseases caused by inflammation in the eye due to an inflammatory causative factor, and the inflammatory ocular disease may include, for example, conjunctivitis, scleritis, keratitis, iritis, uveitis, chorioretinitis, choroiditis, retinitis, and the like, but the present invention is not limited thereto.

The term "ocular disease mediated by an NOD-like receptor pyrin domain-containing protein 3 (NLRP3) inflammasome" refers to an ocular disease occurring by abnormally excessive activation of an NLRP3 inflammasome.

In the present invention, since the vesicles derived from *Micrococcus luteus* can inhibit the activity of an NLRP3 inflammasome, they can be used for a composition for preventing, treating or alleviating an ocular disease mediated by an NLRP3 inflammasome, but the present invention is not limited thereto.

As used herein, the term "extracellular vesicle" or "vesicle" refers to a structure formed of a nano-sized membrane secreted from various bacteria, and includes, for example, a vesicle derived from gram-negative bacteria such as *E. coli*, which has, an endotoxin (lipopolysaccharide), a toxic protein, and both bacterial DNA and RNA, or a vesicle derived from gram-positive bacteria such as bacteria of the genus *Micrococcus*, which have outer membrane vesicles (OMVs), a protein and a nucleic acid as well as components of a bacterial cell wall, such as peptidoglycan and lipoteichoic acid.

In the present invention, the extracellular vesicles or vesicles encompasses all structures which are naturally secreted from *Micrococcus luteus*, or formed of an artificially produced membrane, and in the present invention, the extracellular vesicles or vesicles may be represented by MDH-101, MDH-101 EVs, *M. luteus* EVs or MlEVs.

The vesicles may be isolated by heat treatment or autoclaving during *Micrococcus luteus* culture, or using one or more methods selected from the group consisting of centrifugation, ultracentrifugation, autoclaving, extrusion, sonication, cell lysis, homogenization, freezing-thawing, electroporation, mechanical degradation, chemical treatment, filtration with a filter, gel filtration chromatography, pre-flow electrophoresis, and capillary electrophoresis of the cell culture. In addition, for isolation, washing for removing impurities, and concentration of the obtained vesicles may be further performed.

In the present invention, vesicles isolated by the method are in the form of a sphere, and may have an average diameter 10 to 200 nm, 10 to 190 nm, 10 to 180 nm, 10 to 170 nm, 10 to 160 nm, 10 to 150 nm, 10 to 140 nm, 10 to 130 nm, 10 to 120 nm, 10 to 110 nm, 10 to 100 nm, 10 to 90 nm, 10 to 80 nm, 10 to 70 nm, 10 to 60 nm, 10 to 50 nm, 20 to 200 nm, 20 to 180 nm, 20 to 160 nm, 20 to 140 nm, 20 to 120 nm, 20 to 100 nm, or 20 to 80 nm, preferably 20 to 200 nm, but the average diameter is not limited thereto.

The amount of the vesicles in the composition of the present invention may be appropriately adjusted depending on the symptoms of a disease, the degree of progression of symptoms, the condition of a patient, and the like, and may range from, for example, 0.0001 wt % to 99.9 wt % or 0.001 wt % to 50 wt % with respect to a total weight of the composition, but the present invention is not limited thereto. The amount ratio is a value based on the amount of dried product from which a solvent is removed.

The term "comprised as an active ingredient" used herein refers to comprise a sufficient amount for achieving the efficacy or activity of *Micrococcus luteus*-derived vesicles.

The "pharmaceutical composition" in the present invention is prepared to prevent or treat an ocular disease, and may be formulated in various forms according to conventional methods, respectively. For example, the pharmaceutical composition according to the present invention may be used in an oral formulation such as a powder, a granule, a tablet, a capsule, a suspension, an emulsion or a syrup, a quasi-drug, a suppository, or a sterilized injectable solution.

The pharmaceutical composition according to the present invention may include pharmaceutically acceptable carriers. The pharmaceutically acceptable carrier is generally used in formulation, and includes saline, distilled water, Ringer's solution, buffered saline, cyclodextrin, a dextrose solution, a maltodextrin solution, glycerol, ethanol, liposomes, etc., but the present invention is not limited thereto. If needed, the pharmaceutically composition may further include other conventional additives including an antioxidant, a buffer, etc. In addition, by additionally adding a diluent, a dispersant, a surfactant, a binder or a lubricant, the pharmaceutical composition may be formulated as an injectable form such as an aqueous solution, an emulsion or a suspension, a pill, a capsule, a granule or a tablet. Suitable pharmaceutically acceptable carriers and their formulations may be formulated according to each ingredient using a method disclosed in the Remington's Pharmaceutical Science. The pharmaceutical composition of the present invention is not limited in dosage form, and thus may be formulated as an injection, an inhalant, a dermal preparation for external use, an eye drop, or an oral preparation.

Further, the pharmaceutical composition of the present invention may include an ingredient effective in preventing, alleviating or treating an ocular disease as an active ingredient, other than the vesicles, for example, an antioxidant, or a steroidal or non-steroidal anti-inflammatory drug.

As the antioxidant, ascorbic acid, sodium bisulfite, butylated hydroxytoluene, butylated hydroxyanisole, tocopherol or a combination thereof may be used, but the present invention is not limited thereto.

As the anti-inflammatory drug, dexamethasone, fluorometholone, prednisolone, bromfenac, diclofenac, flubiprofen, ketorolac, or a salt thereof may be used, but the present invention is not limited thereto.

The pharmaceutical composition of the present invention may be administered to an individual via various routes. All administration methods can be predicted, and the pharmaceutical composition may be administered via, for example, oral administration, subcutaneous injection, intraperitoneal administration, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like, and a dose of the pharmaceutical composition may vary depending on the condition and body weight of a patient, the severity of a disease, a drug type, an administration route and time, and may be suitably selected by those of ordinary skill in the art.

In the present invention, the ocular administration may be one selected from the group consisting of intraconjunctival administration, intravitreal administration, subretinal administration, suprachoroidal administration, subconjunctival administration and sub-tenon administration, but the present invention is not limited thereto.

The pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, the effective amount of the composition according to the present invention may vary depending on the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the effective amount may be increased or decreased depending on the administration route, the severity of obesity, gender, body weight, age, and the like, the dosage is not intended to limit the scope of the present invention in any way.

The term "prevention" used herein refers to all actions of inhibiting or delaying the occurrence of an ocular disease by administration of the composition according to the present invention.

The term "treatment" used herein refers to all actions involved in improving or beneficially changing symptoms of an ocular disease by administration of the composition according to the present invention.

The term "alleviation" used herein refers to all actions involved in reducing a parameter associated with a desired disease or a parameter associated with a condition to be treated, for example, the degree of symptoms, by administration of the composition according to the present invention.

In addition, the present invention provides a method for preventing or treating an ocular disease, the method comprising administering the composition to a subject in need thereof.

In addition, the present invention provides a use of vesicles derived from *Micrococcus luteus* for preventing or treating an ocular disease.

In addition, the present invention provides a use of vesicles derived from *Micrococcus luteus* for preparing a drug for treating an age-related ocular disease.

In the present invention, the "subject" refers to a subject in need of treatment of a disease, and more specifically, refers to a mammal such as a human or a non-human primate, a mouse, a rat, a dog, a cat, a horse, and a cow, but the present invention is not limited thereto.

In the present invention, the "administration" refers to providing a subject with a predetermined composition of the present invention by using an arbitrary appropriate method.

In addition, the present invention provides a food composition for preventing or alleviating an ocular disease, comprising vesicles derived from *Micrococcus luteus* as an active ingredient.

The food composition may be a health functional food composition, but is not limited thereto.

The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

The food composition of the present invention has no limitation on components, other than containing the active ingredient as an essential component at an indicated proportion, and may contain various flavoring agents or natural carbohydrates like a conventional beverage. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, *stevia* extract (e.g., rebaudioside A, glycyrrhizin, etc.)] and synthetic sweeteners (saccharin, aspartame, etc.) may be advantageously used. The proportion of the natural carbohydrate may be suitably determined by selection of those of ordinary skill in the art.

Other than the above additives, the food composition of the present invention may contain various nutrients, vitamins, minerals (electrolytes), flavoring agents including synthetic and natural flavoring agents, coloring agents, fillers (cheese, chocolate, etc.), pectic acid and a salt thereof, alginic acid and a salt thereof, organic acids, protective colloidal thickening agents, pH adjustors, stabilizers, preservatives, glycerin, alcohols, or carbonizing agents used in carbonated beverages. Such components may be used independently or in combination. The proportions of these additives may also be suitably selected by those of ordinary skill in the art.

In addition, the present invention provides a quasi-drug composition for preventing or alleviating an ocular disease, comprising vesicles derived from *Micrococcus luteus* as an active ingredient.

The term "quasi-drug" used herein means products exhibiting a milder action than pharmaceuticals among products used for diagnosing, curing, improving, alleviating, treating or preventing a human or animal disease. For example, according to the Pharmaceutical Affairs Act, the quasi-drugs exclude products used as pharmaceuticals, and include textile•rubber products used for treating or preventing human•animal diseases, products which act weakly or do not act directly on the human body, and are not instruments or machines or similar thereto, and sterilizers and insecticides for preventing infectious diseases.

In the present invention, the quasi-drug composition may be formulated as an ophthalmic composition, for example, one or more selected from the group consisting of ophthalmic liquids, eye drops, eye ointments, injection solutions, and eyewashes, but the present invention is not limited thereto.

In addition, the present invention may be provided in the form of an inhalant composition comprising vesicles derived from *Micrococcus luteus* as an active ingredient.

In the case of a preparation for inhalation, the compound may be formulated according to a method known in the art, and may be conveniently delivered in the form of an aerosol spray from a pressurized pack or a nebulizer by using a suitable propellant, for example, dichlorofluoromethane, trichlorofluoromethane, dichlorotetrafluoroethane, carbon dioxide, or other suitable gases. In the case of the pressurized aerosol, a dosage unit may be determined by providing a valve for transferring a metered amount. For example, a gelatin capsule and a cartridge for use in an inhaler or insufflator may be formulated so as to contain a powder mixture of a compound and a suitable powder base such as lactose or starch.

In addition, the present invention provides a composition for delivering a drug for treating an ocular disease, comprising vesicles derived from *Micrococcus luteus* as an active ingredient.

The term "drug delivery" used herein means any means or act of loading and delivering a drug to the composition according to the present invention in order to deliver a drug to a specific organ, tissue, cell or cell organelle.

Modes of the Invention

Hereinafter, preferred Examples for helping the understanding of the present invention will be suggested. However, the following Examples are provided only to more easily understand the present invention, and the contents of the present invention are not limited by the following Examples.

EXAMPLES

Example 1. Isolation of Vesicles from *Micrococcus luteus* Culture Fluid

After culturing a *Micrococcus luteus* strain, vesicles thereof were isolated, analyzed and characterized. *Micrococcus luteus* was cultured in a de Man-Rogosa and Sharpe (MRS) medium until absorbance (OD 600) became 1.0 to 1.5 in a 37° C. aerobic chamber, and then sub-cultured. Subsequently, the medium supernatant containing the strain was recovered, centrifuged at 10,000 g and 4° C. for 20 minutes, and the strain was removed and then filtered through a 0.22-μm filter. And the filtered supernatant was concentrated to a volume of 50 mL using a 100 kDa Pellicon 2 Cassette filter membrane (Merck Millipore, US) and a MasterFlex pump system (Cole-Parmer, US) through microfiltration. Then, the concentrated supernatant was filtered again using a 0.22 μm filter. Subsequently, the protein was quantified using a BCA assay, and the following experiments were performed on the obtained vesicles.

Example 2. Evaluation of Pharmacokinetic Characteristics of Vesicles Derived from *Micrococcus luteus*

In order to investigate the pharmacokinetic characteristics of vesicles derived from *Micrococcus luteus* during oral administration, the fluorescence expressed in the body and each organ from immediately before administration to 72 hours after administration was measured by orally administering vesicles derived from *Micrococcus luteus* stained with a fluorescent staining reagent to mice.

As shown in FIG. 1, when long-term distribution over time of fluorescence-stained vesicles derived from *Micrococcus luteus* was confirmed with an image, it can be confirmed that the vesicles were distributed in several organs.

Figure 2:
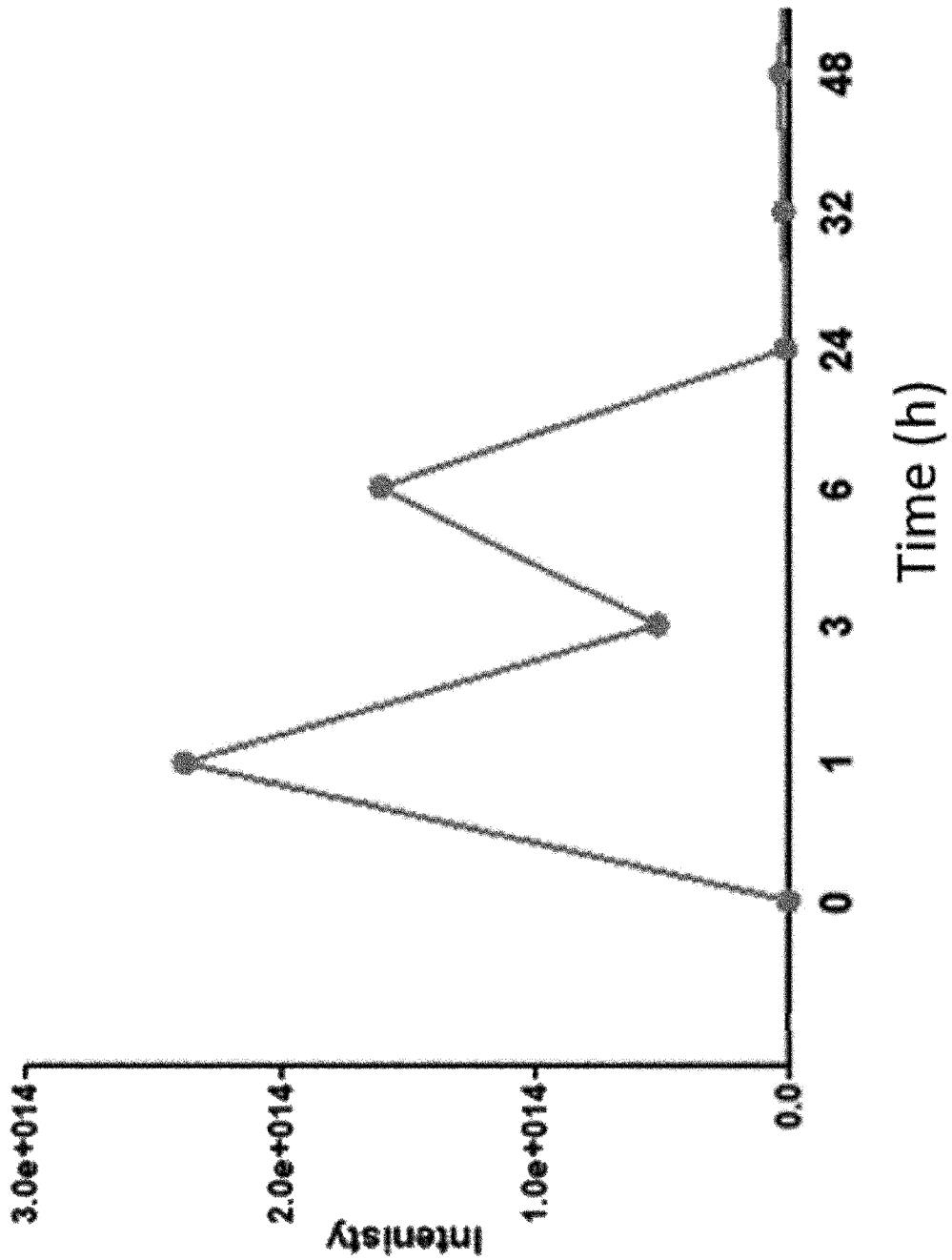
FIG. 2 shows the pattern of distributing *Micrococcus luteus*-derived vesicles in the brain over time after the vesicles are orally administered to mice.

In addition, when the fluorescence intensity of extracellular vesicles derived from *Micrococcus luteus* expressed in the brain was plotted in a graph, as shown in FIG. 2, it was confirmed that a signal of the vesicles in the brain was shown one hour after oral administration and continued until 24 hours, and then the fluorescence signal disappeared.

From the result, it can be seen that, when orally administered, the vesicles derived from *Micrococcus luteus* were absorbed into the body through a mucous membrane, and distributed in various organs, and particularly, they migrated to the central nervous system including the retina through the BBB and distributed.

Figure 3:
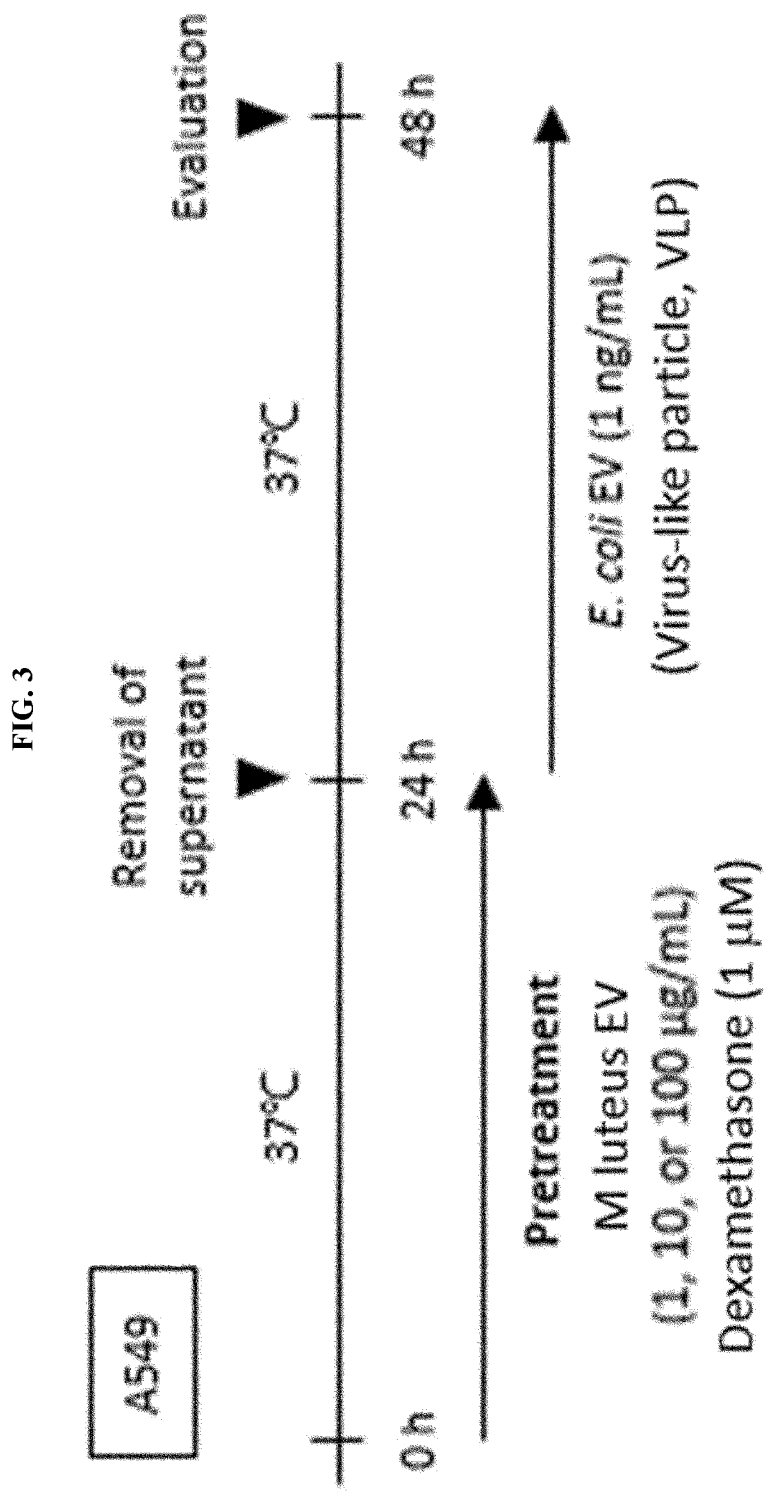
FIG. 3 shows an experimental protocol for evaluating an anti-inflammatory effect of *Micrococcus luteus*-derived vesicles (*M. luteus* EVs) in epithelial cells.

Example 3. Evaluation of Anti-Inflammatory Effect of Vesicles Derived from *Micrococcus luteus* in Epithelial Cells As shown in FIG. 3, epithelial cells (A549 cells) were pre-treated with vesicles derived from *Micrococcus luteus* (*M. luteus* EV) and a positive control drug, dexamethasone, and after treatment with vesicles derived from *E. coli* (*E. coli* EVs) inducing inflammation, a secretion level of an inflammatory cytokine such as IL-8 was measured using enzyme-linked immunosorbent assay (ELISA, R&D Systems). Specifically, A549 cells were pre-treated with vesicles derived from *Micrococcus luteus* at various concentrations (1, 10 and 100 ng/mL) for 24 hours, and then treated with vesicles derived from *E. coli* at a concentration of 1 ng/mL for 24 hours, followed by measuring IL-8 secreted into the medium.

Figure 4A:
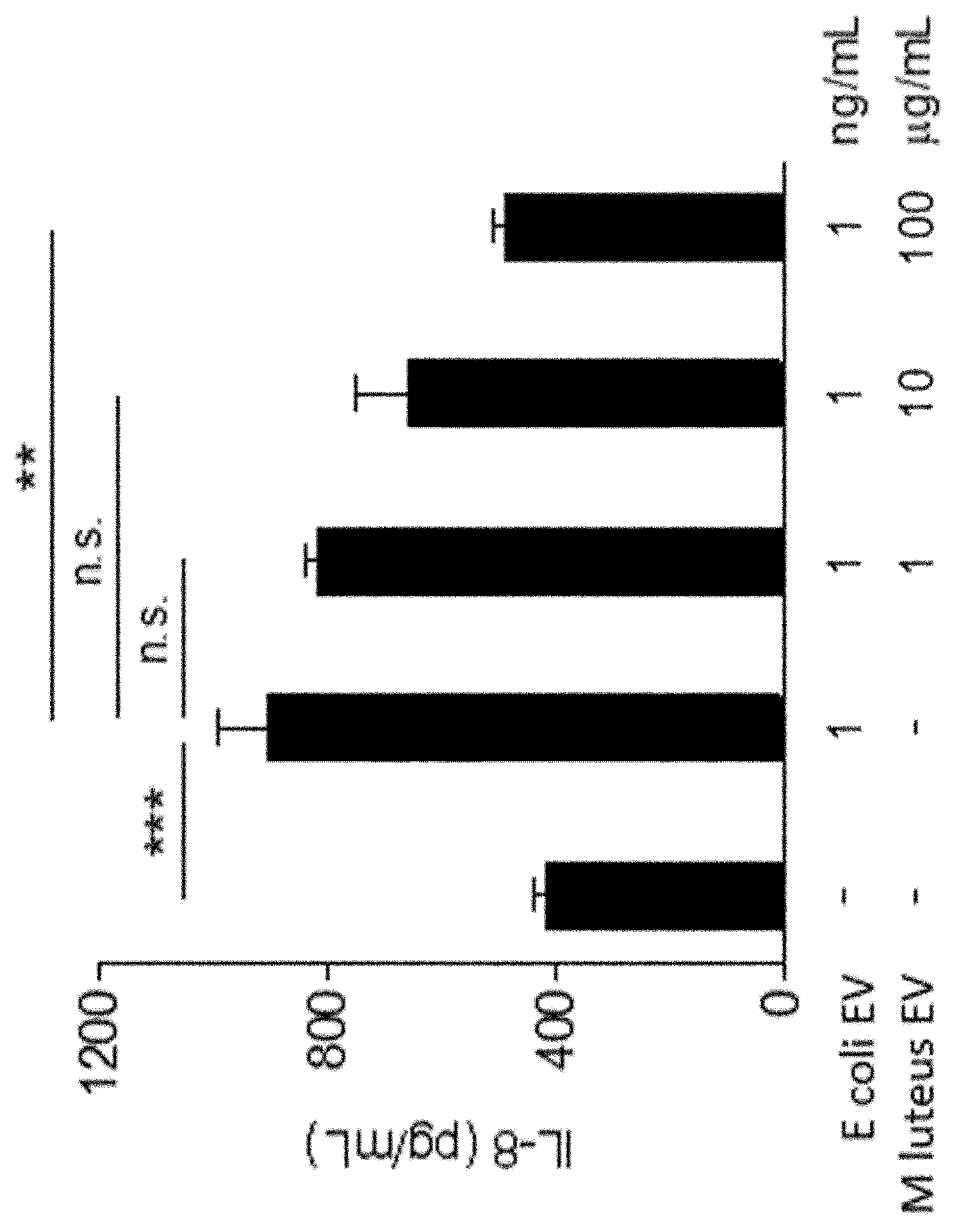
FIGS. 4A and 4B are results of treating epithelial cells with *Micrococcus luteus*-derived vesicles (*M. luteus* EVs) and a positive control drug, dexamethasone (Dex) to evaluate an anti-inflammatory effect of *Micrococcus luteus*-derived vesicles (*M. luteus* EVs)
Figure 4B:
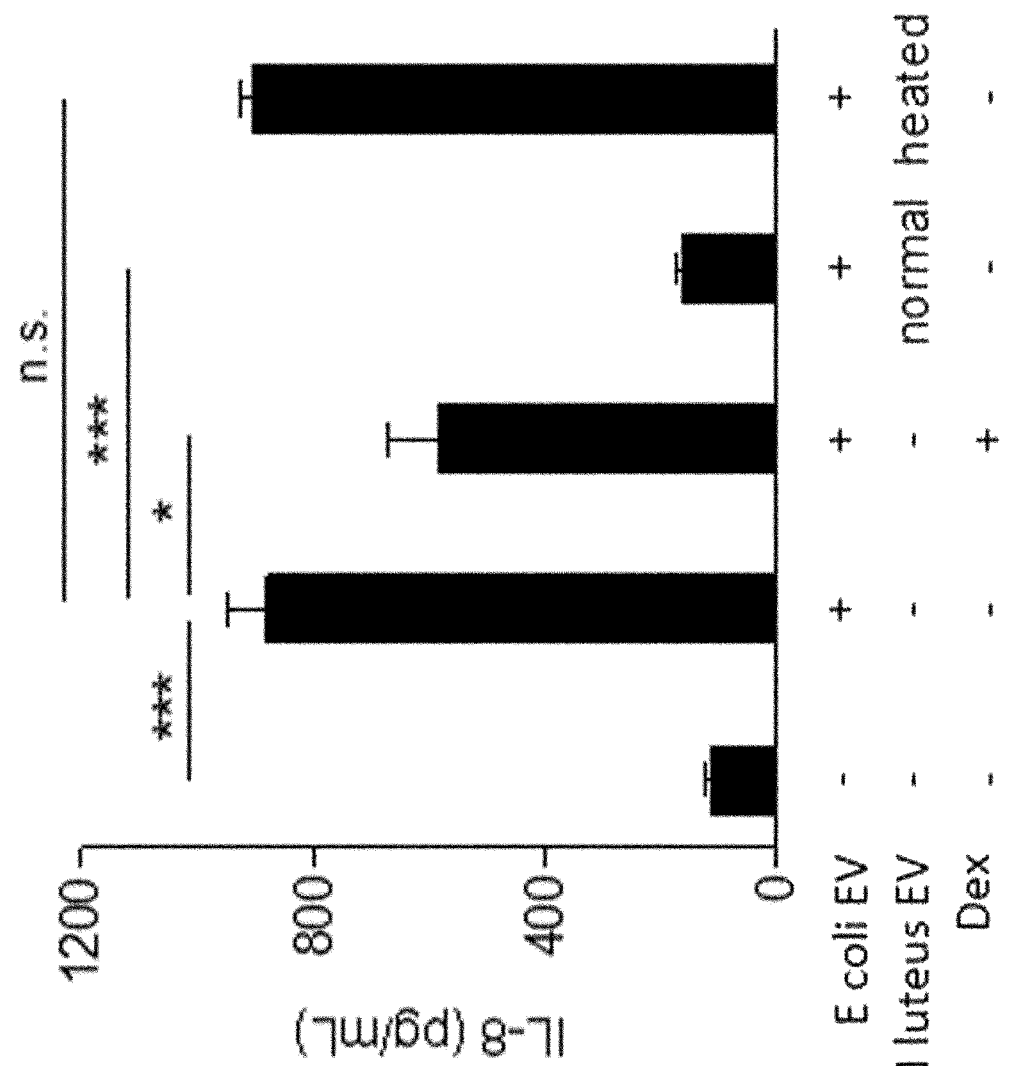

As a result, as shown in FIG. 4A, it was confirmed that IL-8 secretion was inhibited by the vesicles derived from *Micrococcus luteus* in a dose-dependent manner. In addition, as shown in FIG. 4B, it was confirmed that, when compared with a control drug, dexamethasone, the IL-8 secretion inhibitory effect was more excellent, and when the extracellular vesicles were administered after heat treatment, the IL-8 secretion inhibitory effect disappeared. From the above result, it can be seen that, compared to the representative anti-inflammatory drug, dexamethasone, the vesicles derived from *Micrococcus luteus* have a more excellent anti-inflammatory effect, the anti-inflammatory effect mediated by the vesicles derived from *Micrococcus luteus* disappeared after heat treatment, indicating that the anti-inflammatory action is mediated by a protein in the extracellular vesicles.

Figure 5:
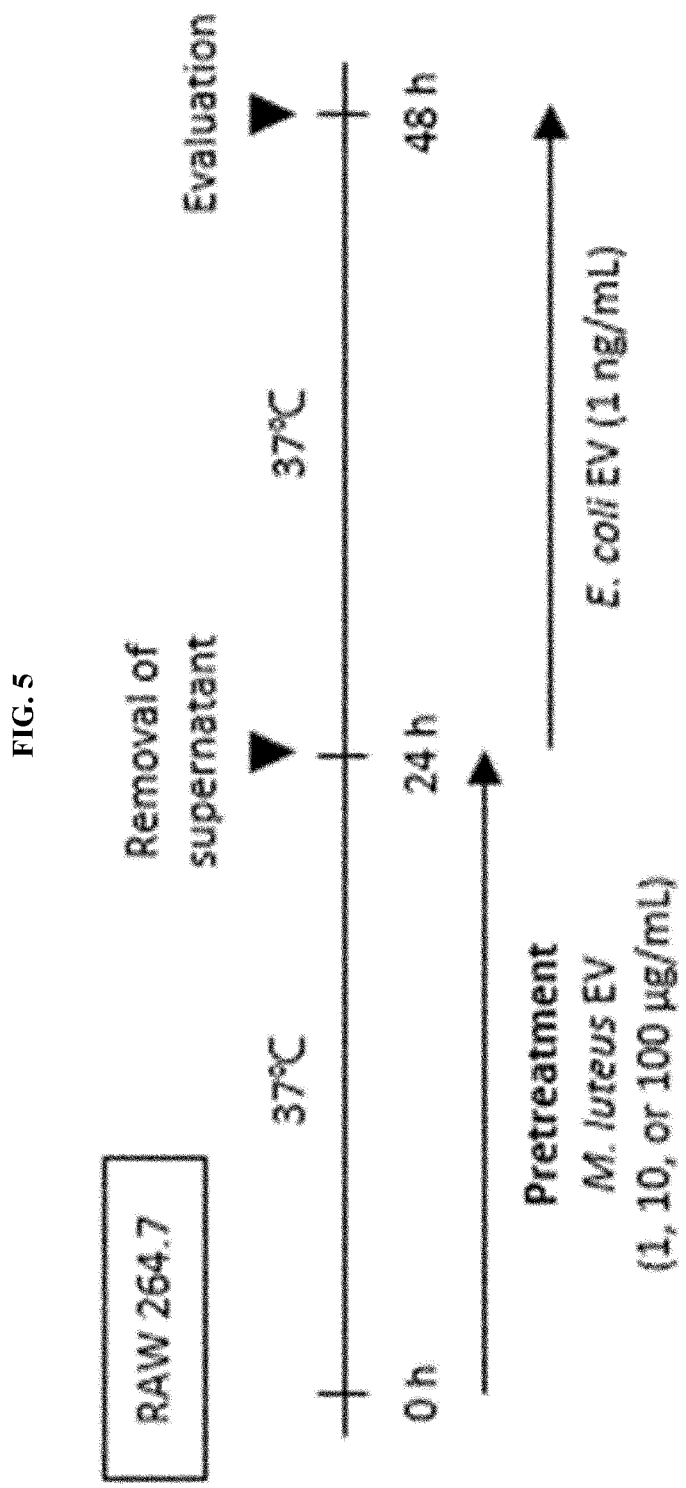
FIG. 5 shows an experimental protocol for evaluating an anti-inflammatory effect of *Micrococcus luteus*-derived vesicles (*M. luteus* EVs) in macrophages.

Example 4. Evaluation of Anti-Inflammatory Effect of Vesicles Derived from *Micrococcus luteus* in Inflammatory Cells Such as Macrophages As shown in FIG. 5, macrophages (RAW 264.7 cells) were pre-treated with vesicles derived from *Micrococcus luteus* (*M. luteus* EVs), and then treated with vesicles derived from *E. coli* (*E. coli* EVs) inducing inflammation, followed by measuring levels of inflammatory cytokines, such as TNF-α and IL-6, through ELISA (R&D Systems). Specifically, after pre-treatment with vesicles derived from *Micrococcus luteus* at various concentrations (1 μg/mL, 10 μg/mL, and 100 μg/mL) for 24, hours, and treatment with vesicles derived from *E. coli* at 1 ng/mL for 24 hours, TNF-α and IL-6 secreted into the medium were measured.

Figure 6A:
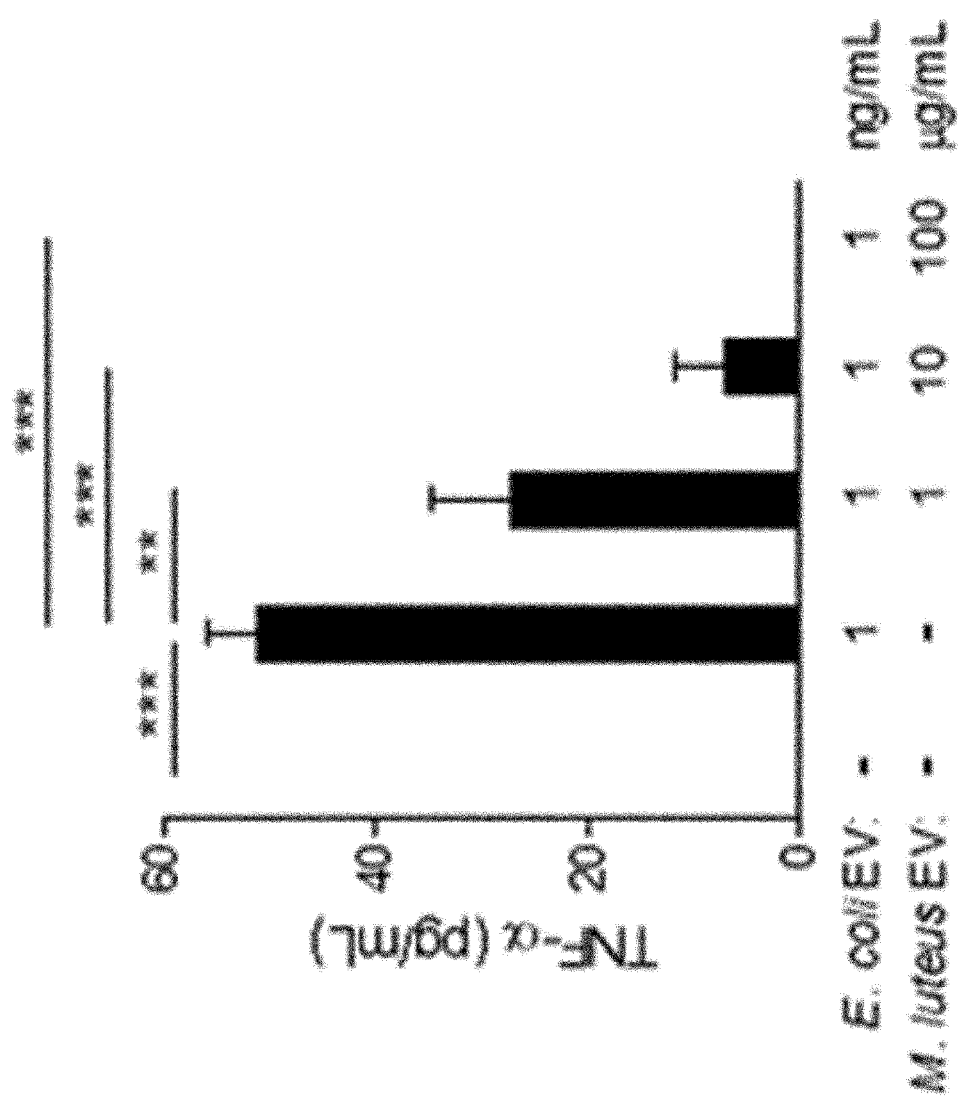
FIGS. 6A and 6B are results of treating macrophages with *Micrococcus luteus*-derived vesicles (*M. luteus* EVs) to evaluate an anti-inflammatory effect of *Micrococcus luteus*-derived vesicles (*M. luteus* EVs)
Figure 6B:
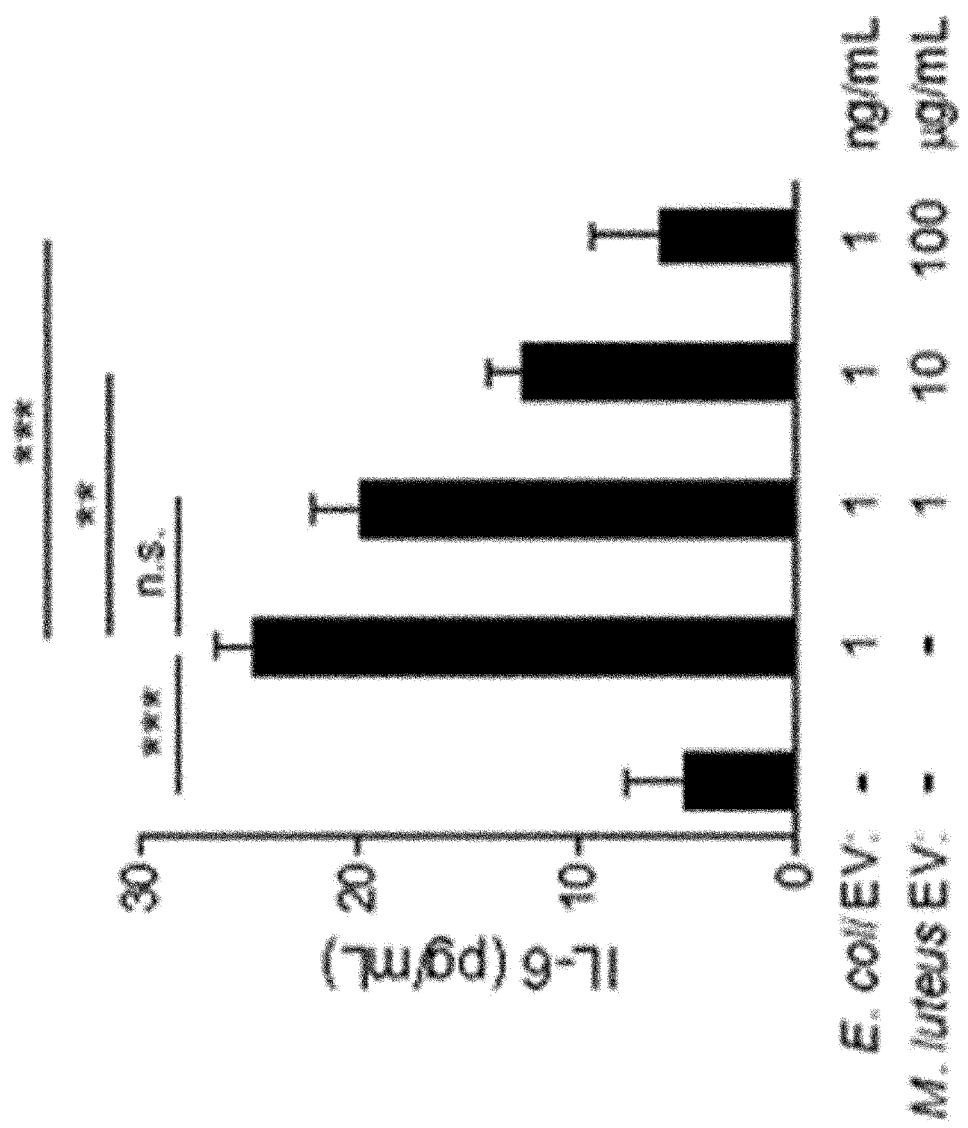

As a result, as shown in FIGS. 6A and 6B, it was confirmed that, when the vesicles derived from *Micrococcus luteus* were pre-treated, the secretion of TNF-α (FIG. 6A) and IL-6 (FIG. 6B) by the vesicles derived from *E. coli* was inhibited in a dose-dependent manner. This result shows that inflammation caused by pathogenic biological causative factors (pathogenic bacteria or viruses) is effectively inhibited by the vesicles derived from *Micrococcus luteus*.

Figure 7:
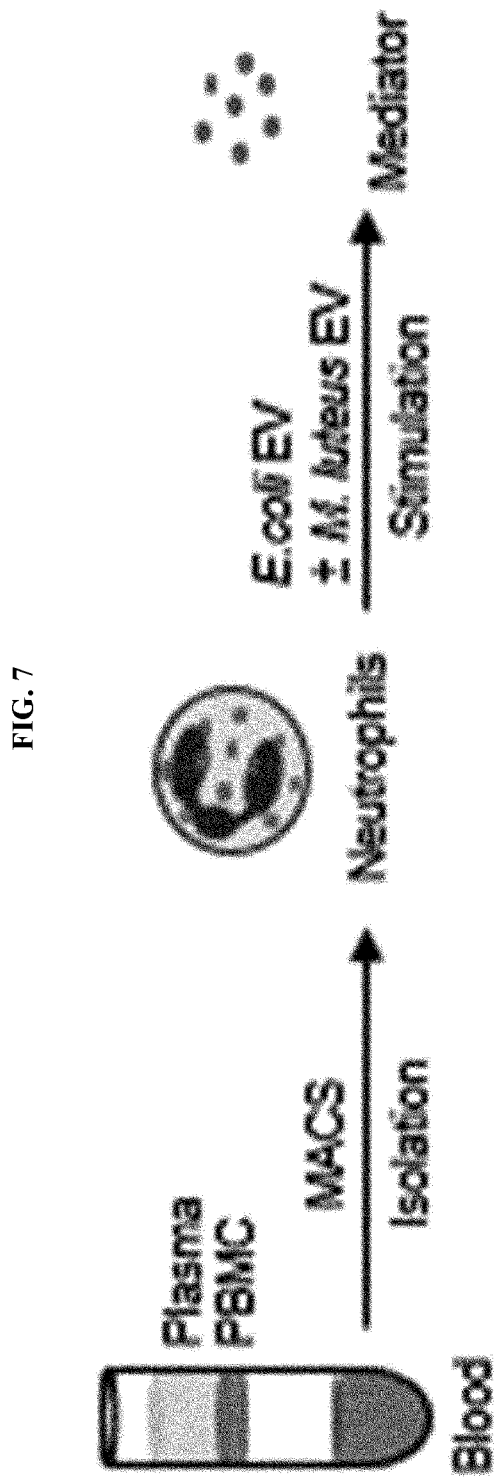
FIG. 7 is an experimental protocol evaluating a degree of neutrophil activation by *E. coli*-derived vesicles (*E. coli* EVs), which is a biological causative factor, by treating neutrophils isolated from peripheral blood with *Micrococcus luteus*-derived vesicles (*M. luteus* EVs) or a positive control drug, dexamethasone.

Example 5. Evaluation of Neutrophil Activation Inhibitory Effect of Vesicles Derived from *Micrococcus luteus* in Inflammatory Cells Such as Neutrophils As shown in FIG. 7, human blood was isolated using Lymphoprep to extract neutrophils, and to evaluate neutrophil activation, a granular protein such as neutrophil elastase (NE) in the neutrophils was measured by ELISA (R&D Systems). Specifically, 10 mL of blood was collected in a tube containing an ACD solution, the blood was carefully added over 20 mL of Lymphoprep and centrifuged. After centrifugation, a red blood layer was collected and mixed with 12 mL of dextran, followed by standing at room temperature for 45 minutes. After layer separation, 40 mL of 1×HBSS was added to the supernatant and centrifuged again, and red blood cells were removed with autoclaved Millipore water, and then neutrophils were isolated using a neutrophil isolation kit (MACS). The isolated neutrophils were cultured using an RPMI1640 medium, and treated with both vesicles derived from *E. coli* (*E coli* EVs) and vesicles derived from *Micrococcus luteus* (*M. luteus* EVs) for 24 hours, followed by measuring NE in the medium. As a positive control drug, dexamethasone (Dex) was treated.

Figure 8:
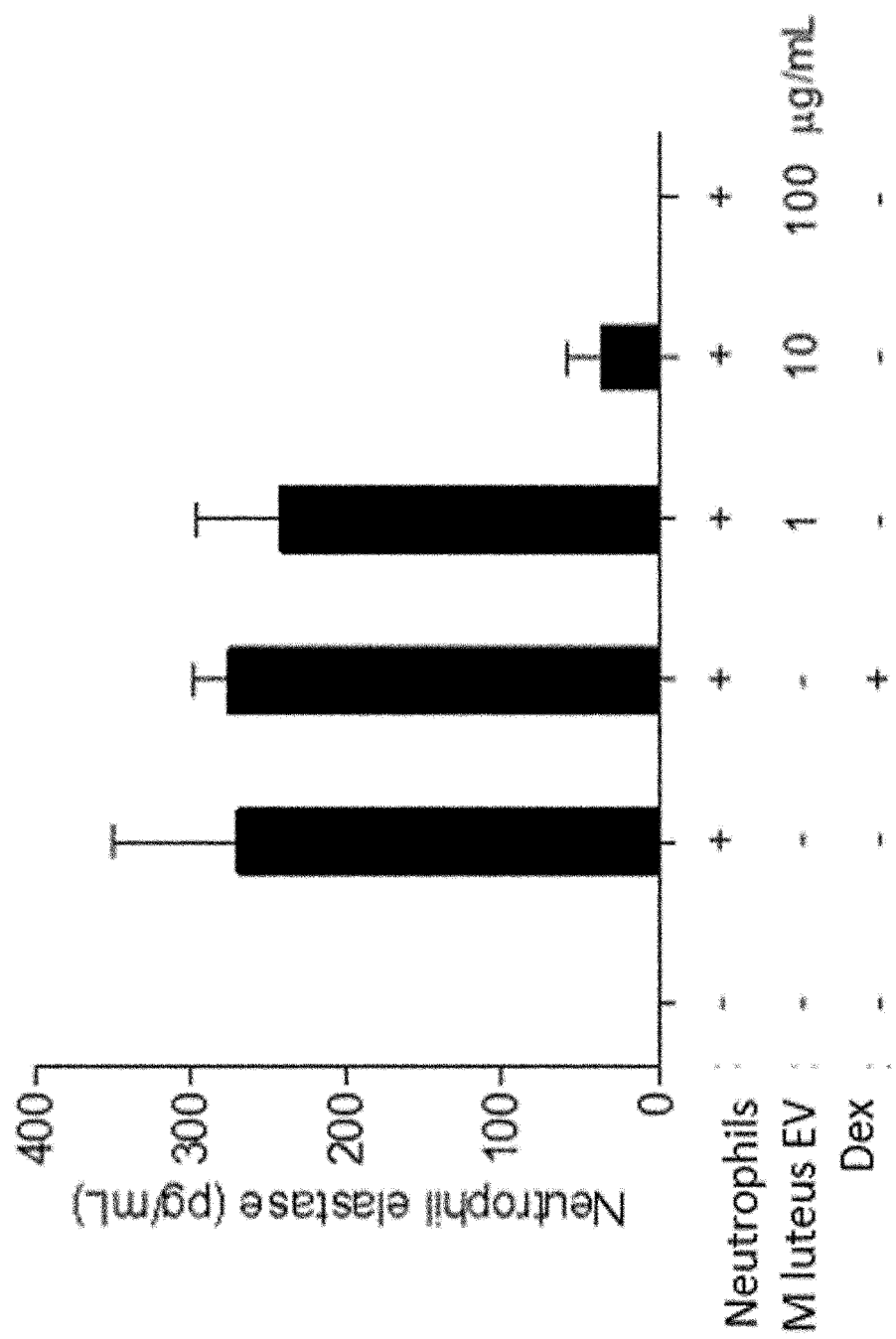
FIG. 8 is a result of evaluating a degree of neutrophil activation by *E. coli*-derived vesicles (*E. coli* EVs), which are pathogenic nanoparticles, by neutrophil elastase (NE) secretion when neutrophils isolated from peripheral blood are treated with *Micrococcus luteus*-derived vesicles (*M. luteus* EVs) and a positive control drug, dexamethasone.

As a result, as shown in FIG. 8, the control drug, dexamethasone, did not inhibit secretion of NE, which is a neutrophil activation indicator, but the vesicles derived from *Micrococcus luteus* inhibited NE secretion in neutrophils in a dose-dependent manner. From the above result, it can be seen that the vesicles derived from *Micrococcus luteus* can efficiently treat a disease occurring by neutrophil activation.

Figure 9:
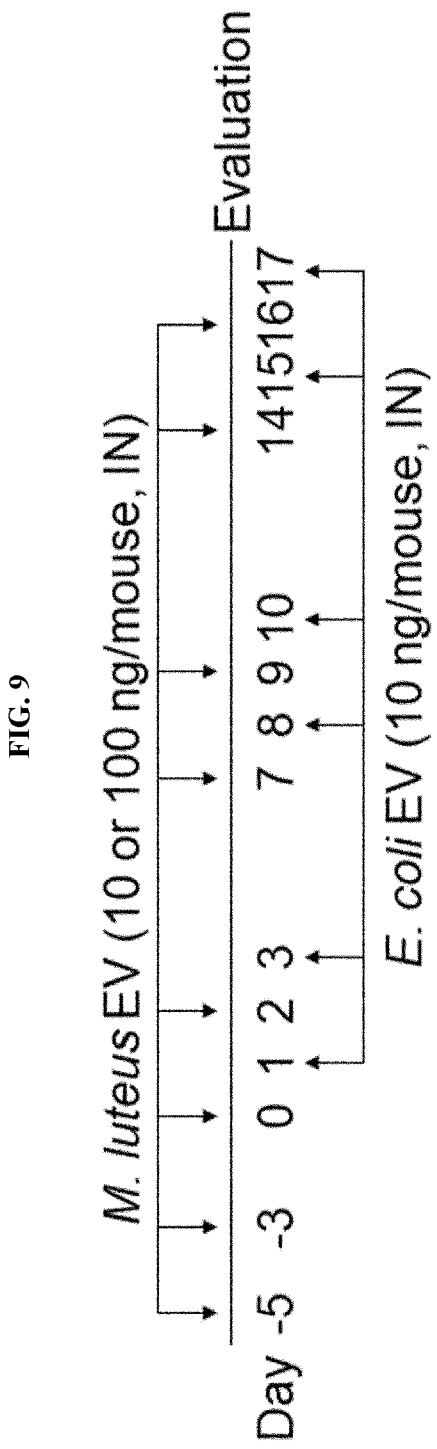
FIG. 9 is an experimental protocol for confirming an inflammatory disease inhibitory effect and a mechanism of action thereof caused by *Micrococcus luteus*-derived vesicles (*M. luteus* EVs) in mouse models with an inflammatory disease caused by *E. coli*-derived vesicles (*E. coli* EVs), which are pathogenic nanoparticles.

Example 6. Evaluation of Anti-Inflammatory Effect of Vesicles Derived from *Micrococcus luteus* in Mouse Model with Inflammatory Disease Caused by Pathogenic Nanoparticles As shown in FIG. 9, a mouse model with an inflammatory disease was prepared by intranasally administering 10 ng/ml of pathogenic nanoparticles, such as vesicles derived from *E. coli* (*E. coli* EVs). To evaluate an immune function-regulatory effect of vesicles derived from *Micrococcus luteus* in the model, anti-inflammatory effects in bronchoalveolar lavage fluid (BALF) and lung tissue were evaluated by intranasally administering 10 ng/ml or 100 ng/ml of vesicles derived from *Micrococcus luteus* 5 days before administration of the vesicles derived from *E. coli*. Specifically, to evaluate an anti-inflammatory effect in the bronchoalveolar lavage fluid (BALF), a syringe containing 1 mL of PBS was connected to the airway to collect the bronchoalveolar lavage fluid (BALF), and the numbers of total cells, macrophages and neutrophils were measured using Trypan blue (Abcam). In addition, to evaluate an anti-inflammatory effect in lung tissue, slide glasses were mounted on Cytopro (ELItech) to fix the cells, and a neutrophil number was measured after staining with Hematoxylin (DAKO) and Eosin (Sigma, USA).

Figure 10A:
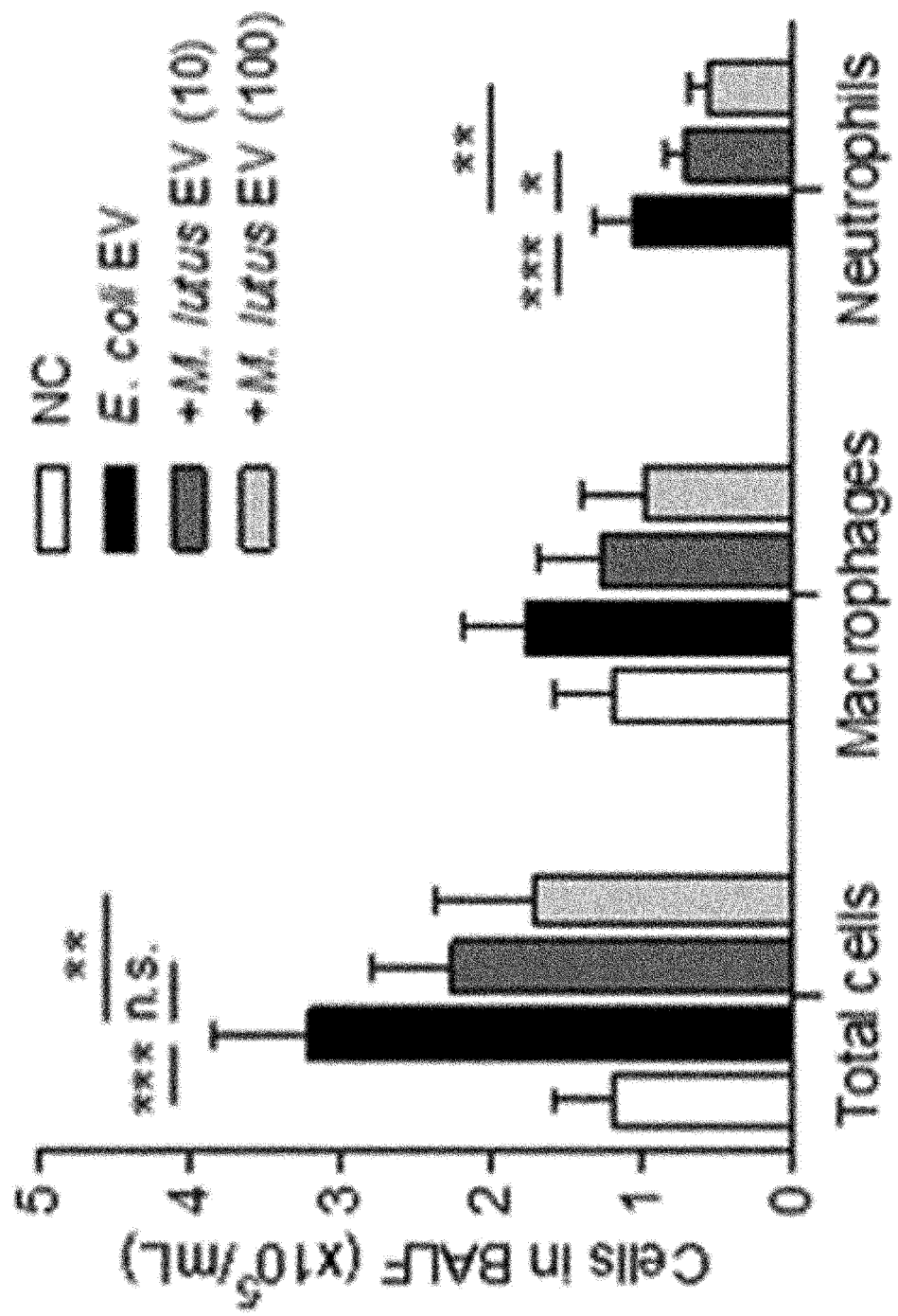
FIGS. 10A and 10B show an inflammatory inhibitory effect of *Micrococcus luteus*-derived vesicles (*M. luteus* EVs) in mouse models with an inflammatory disease caused by *E. coli*-derived vesicles (*E. coli* EVs), which are pathogenic nanoparticles.
Figure 10B:
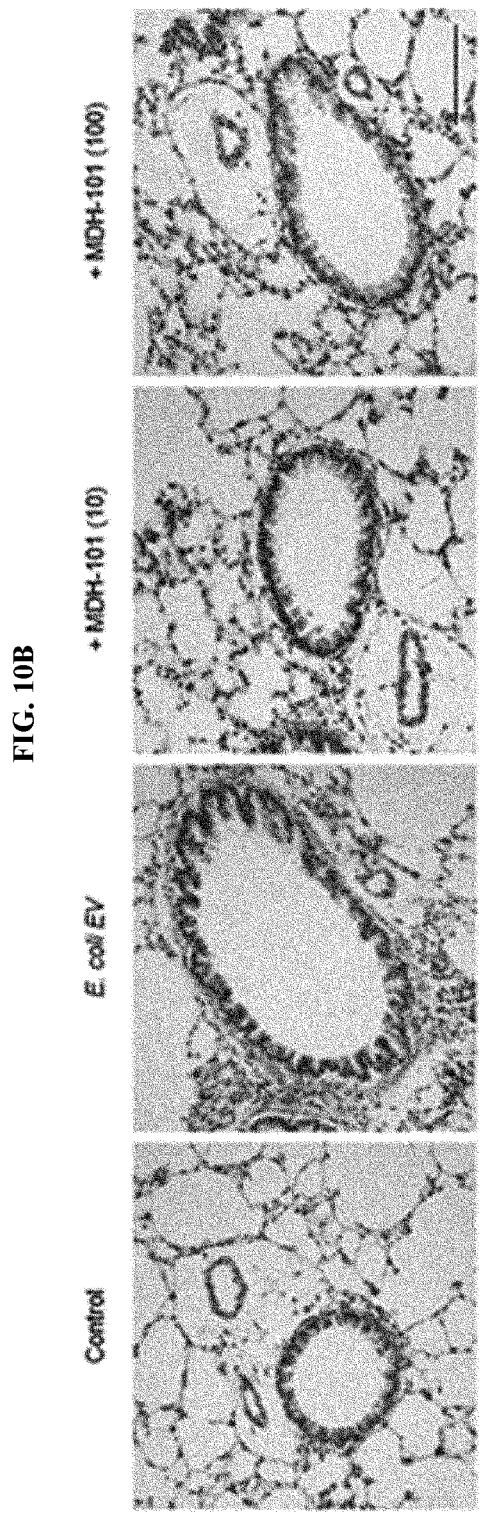

As a result, as shown in FIG. 10A, in the bronchoalveolar lavage fluid (BALF) from the group to which the vesicles derived from *Micrococcus luteus* are administered, it was confirmed that the numbers of macrophages and neutrophils are reduced in a dose-dependent manner. In addition, as shown in FIG. 10B, as a result of evaluating a histological change in the lungs using Hematoxylin & Eosin staining, it was confirmed that the infiltration of immune cells and inflammatory cells was significantly reduced in the lung tissue of the group to which vesicles derived from *Micrococcus luteus* are administered.

Figure 11A:
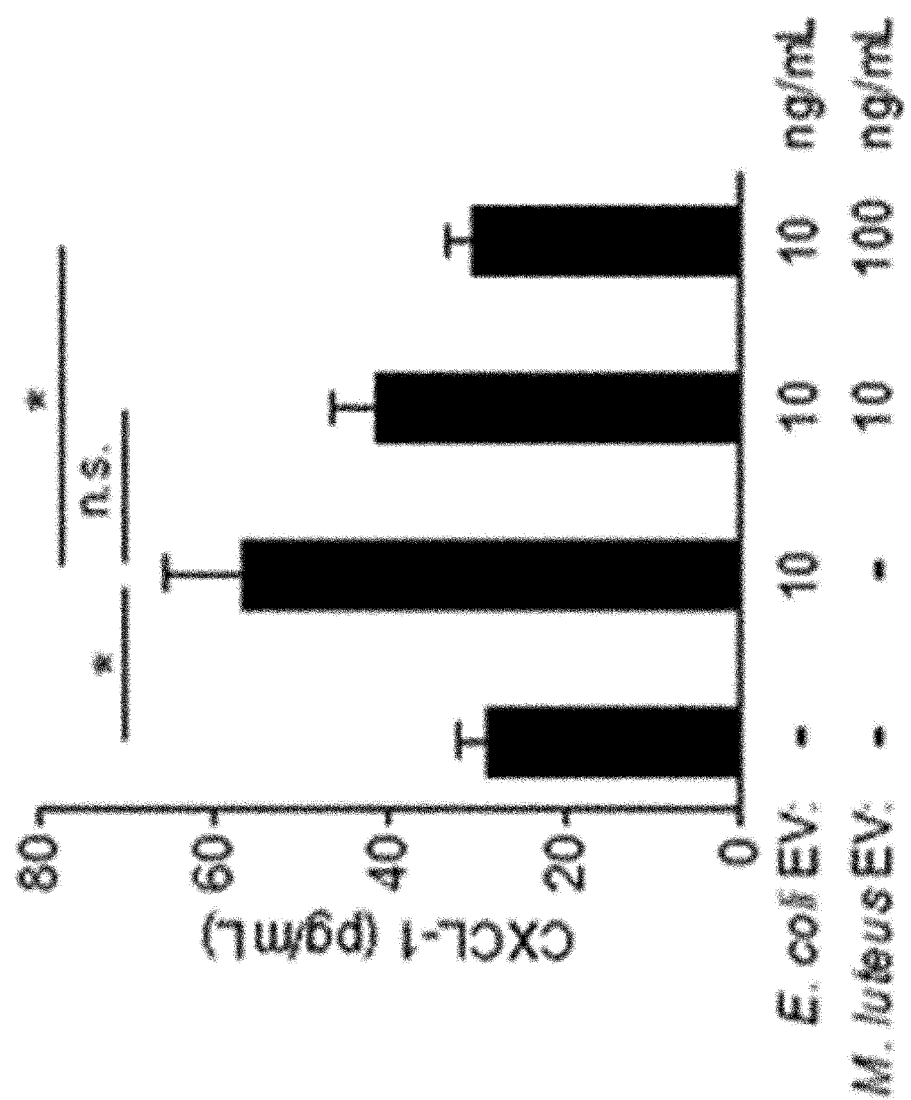
FIGS. 11A to 11C show inhibitory effect on secretion of an inflammatory mediator by *Micrococcus luteus*-derived vesicles (*M. luteus* EVs) in mouse models with an inflammatory disease caused by *E. coli*-derived vesicles (*E. coli* EVs), which are pathogenic nanoparticles.
Figure 11B:
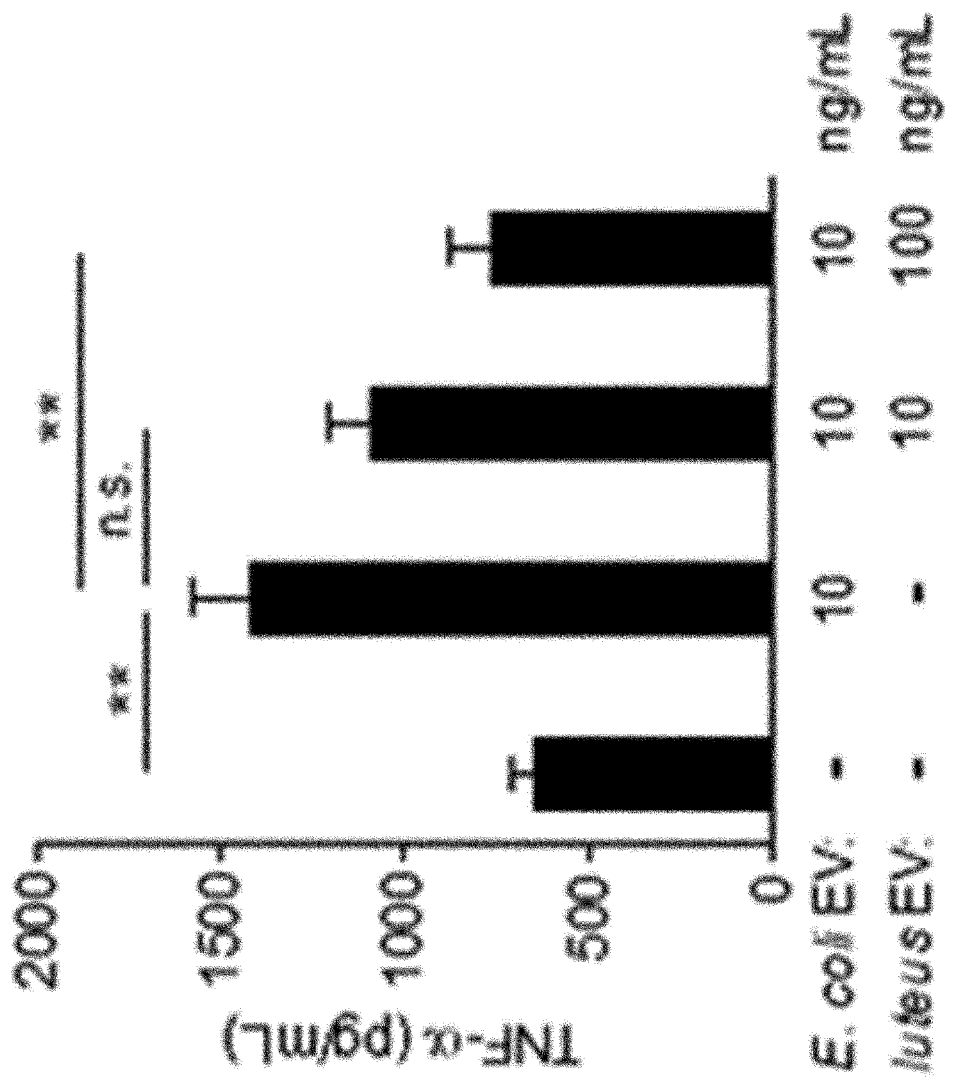
Figure 11C:
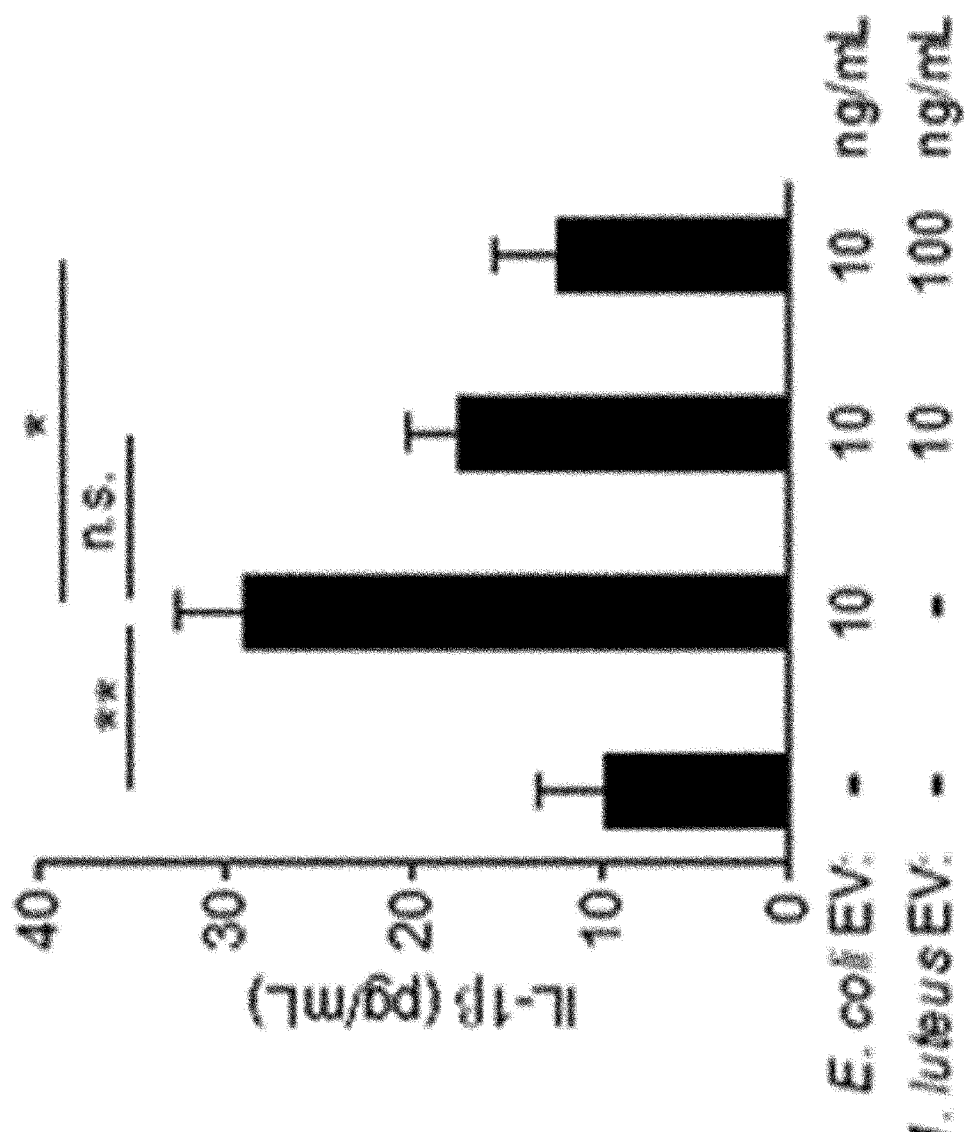

Further, as shown in FIGS. 11A to 11C, the evaluation of the degree of inflammatory mediator secretion in the bronchoalveolar lavage fluid (BALF) showed that the secretion of inflammation-inducing cytokines, such as CXCL-1 (FIG. 11A), TNF-α (FIG. 11B) and IL-1β (FIG. 11C), was inhibited by the vesicles derived from *Micrococcus luteus* in a dose-dependent manner.

From the above result, it was seen that the vesicles derived from *Micrococcus luteus* can efficiently inhibit an inflammatory disease caused by pathogenic nanoparticles.

Example 7. Evaluation of Immunomodulatory Effect of Vesicles Derived from *Micrococcus luteus* in Mouse Model with Inflammatory Disease Caused by Pathogenic Nanoparticles An immunomodulatory effect was evaluated by administering vesicles derived from *Micrococcus luteus* into the mouse model with an inflammatory disease of Example 6.

Figure 12A:
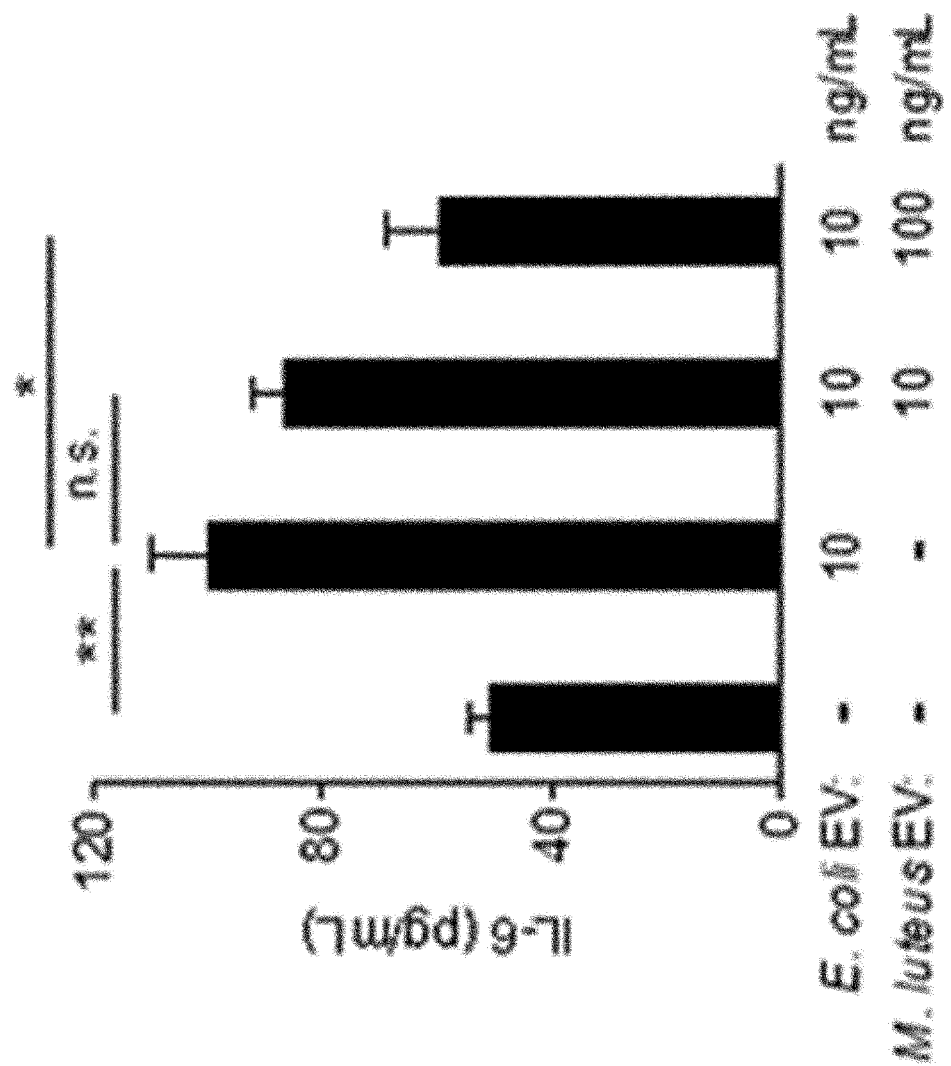
FIGS. 12A to 12C show an effect of *Micrococcus luteus*-derived vesicles (*M. luteus* EVs) on secretion of an immunomodulation-associated cytokine in mouse models with an inflammatory disease caused by *E. coli*-derived vesicles (*E. coli* EVs), which are pathogenic nanoparticles.
Figure 12B:
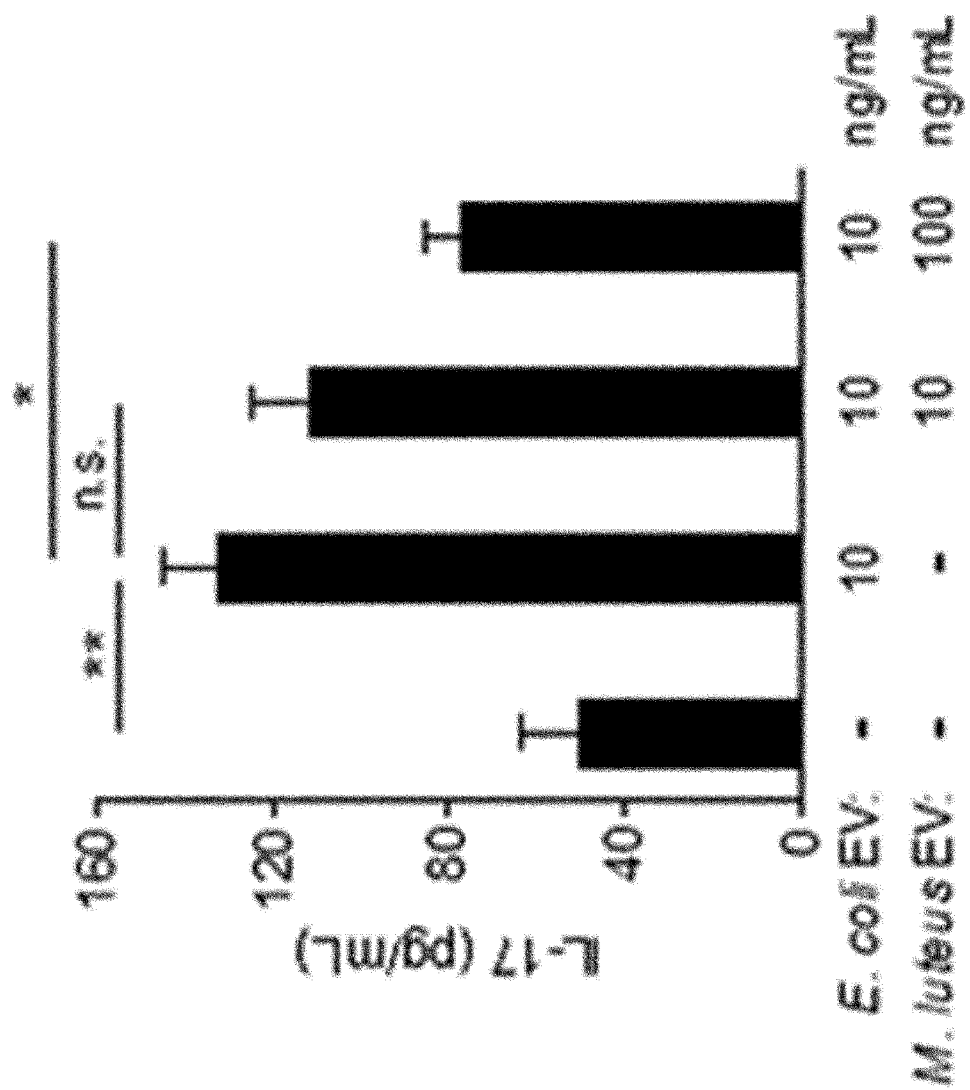

As a result, as shown in FIGS. 12A and 12B, it was confirmed that the secretion of cytokines such as IL-6 (FIG. 12A) and IL-17 (FIG. 12B) associated with an immune response causing inflammation by vesicles derived from *E. coli* is inhibited by the vesicles derived from *Micrococcus luteus* in a dose-dependent manner.

Figure 12C:
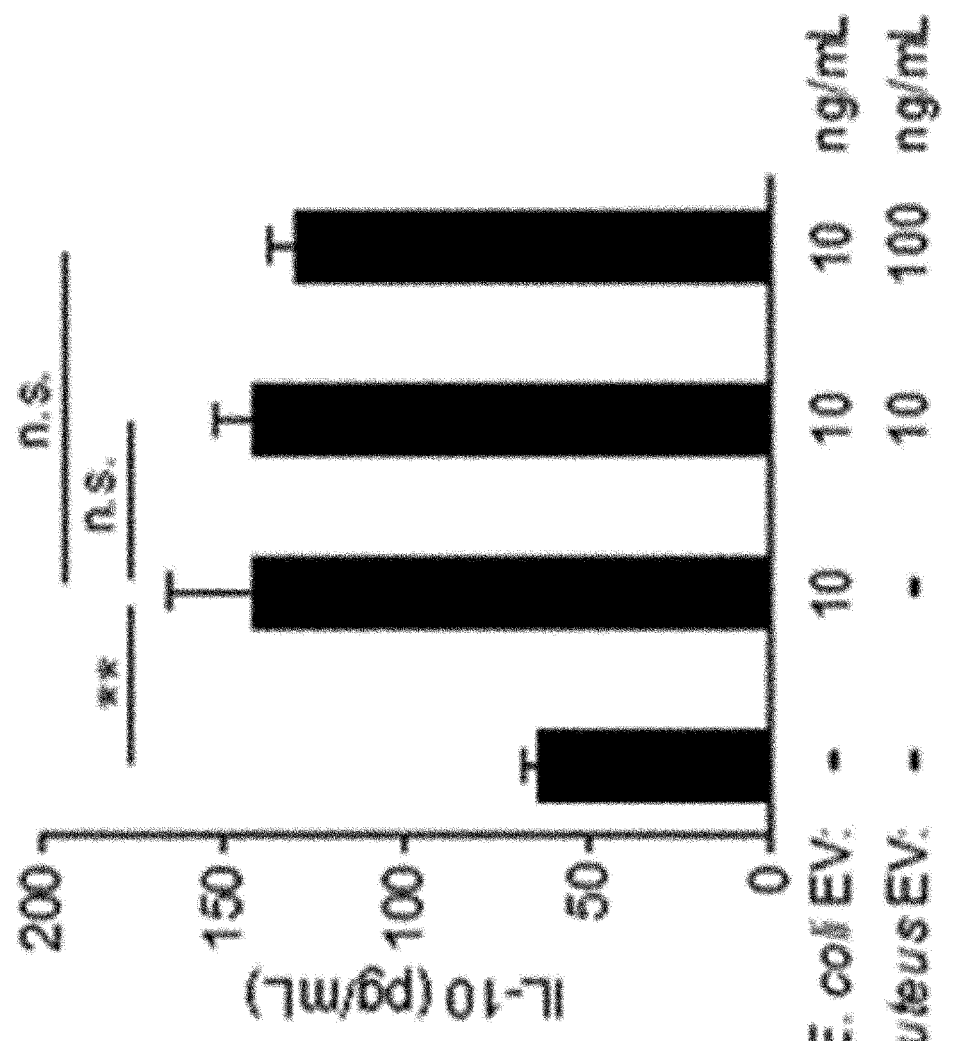

On the other hand, as shown in FIG. 12C, the secretion of a cytokine IL-10, which inhibits immune function, was not inhibited by vesicles derived from *Micrococcus luteus* (FIG. 12C). From the above result, it can be seen that an anti-inflammatory effect caused by the vesicles derived from *Micrococcus luteus* is exhibited by inhibiting an immune response by pathogenic nanoparticles.

Example 8. Evaluation of Therapeutic Effect of Vesicles Derived from *Micrococcus Luteus* in Mouse Model with Inflammatory Disease Caused by Virus-Mimicking Pathogenic Nanoparticles on Abnormal Immune Function The inflammatory response caused by abnormal immune function causes a functional change in an organ, causing a disease. The functional change in the lungs induced by inflammation was evaluated by administering the vesicles derived from *Micrococcus luteus* into the mouse model with an inflammatory disease of Example 6. Specifically, the functional change was evaluated by administering aerosol methacholine (Sigma, USA) into each mouse at various concentrations (0 mg/mL, 6.25 mg/mL, 12.5 mg/mL and 25 mg/mL), and measuring airway hyper-responsiveness (AHR) to methacholine by measuring the maximum airway responsiveness to methacholine inhaled using flexiVent (SCIREQ, Canada).

Figure 13:
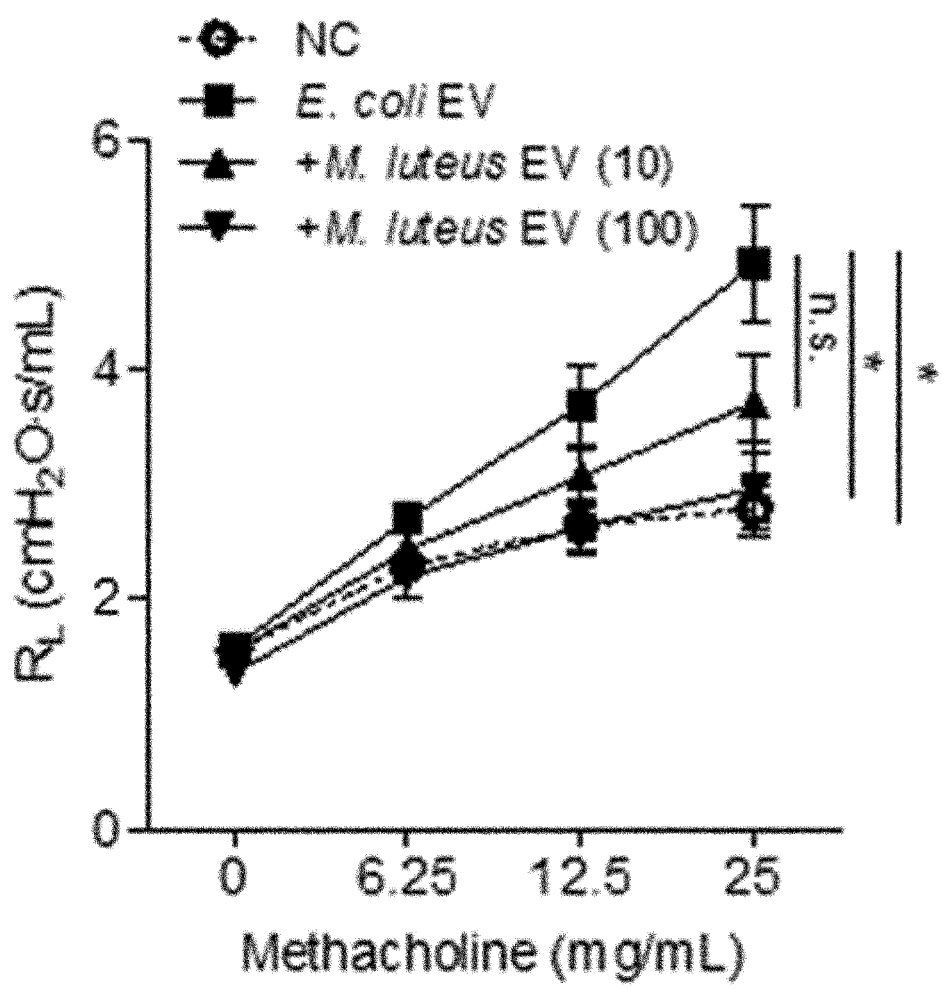
FIG. 13 shows an effect of *Micrococcus luteus*-derived vesicles (*M. luteus* EVs) on airway hyper-responsiveness in mouse models with an inflammatory disease caused by *E. coli*-derived vesicles (*E. coli* EVs), which are pathogenic nanoparticles.

As a result, as shown in FIG. 13, it was confirmed that the airway hyper-responsiveness (AHR) induced by methacholine is improved in a dose-dependent manner in a group to which the vesicles derived from *Micrococcus luteus* are administered. From the above result, it can be seen that a change in immune function associated with inflammation among causes of a disease induced by pathogenic nanoparticles can be effectively treated by the vesicles derived from *Micrococcus luteus*.

Figure 14:
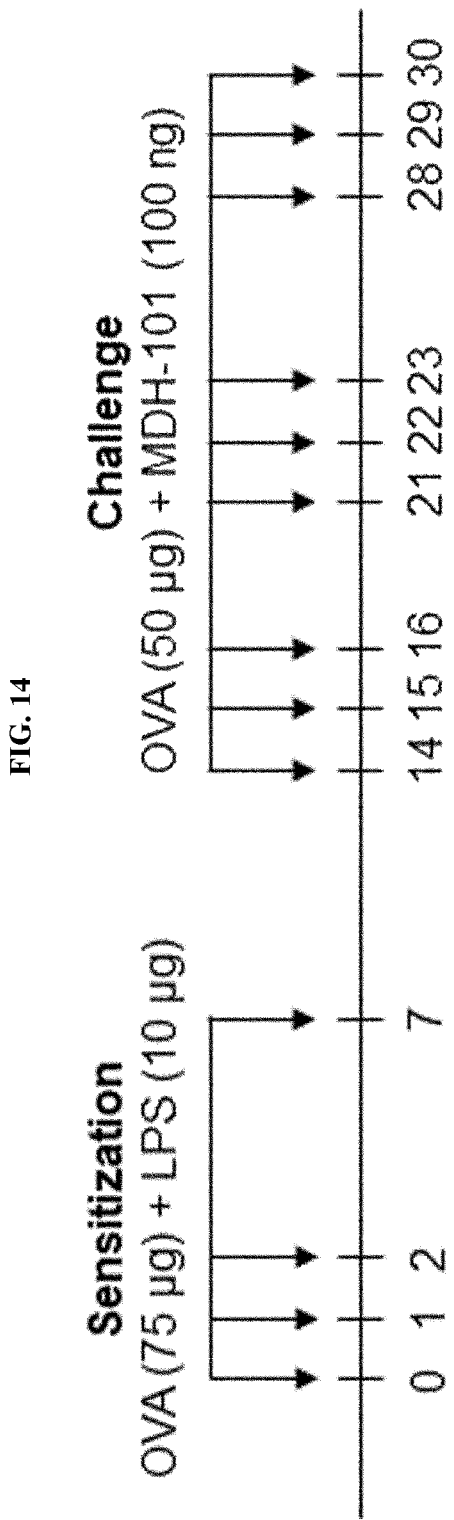
FIG. 14 shows an experimental protocol for evaluating an effect of *Micrococcus luteus*-derived vesicles (*M. luteus* EVs) on treatment of an inflammatory disease in mouse models with an immune disease caused by a protein contaminated by LPS.

Example 9. Evaluation of Anti-Inflammatory Effect of Vesicles Derived from *Micrococcus luteus* in Mouse Model with Immune Disease Caused by Protein Contaminated by LPS As shown in FIG. 14, to prepare a mouse model with an immune disease caused by a protein contaminated by LPS, 10 µg of LPS, which is one of the pathogen-associated molecular patterns (PAMPs) derived from a biological causative factor, and 75 µg of ovalbumin (OVA) protein were inhaled into a mouse, thereby preparing a mouse model with an immune disease caused by a protein contaminated by LPS. Afterward, both 50 µg of OVA and 100 ng of vesicles derived from *Micrococcus luteus* were administered intranasally for 3 weeks. As a control drug, 20 µg of dexamethasone (Dex) was intraperitoneally administered.

Figure 15A:
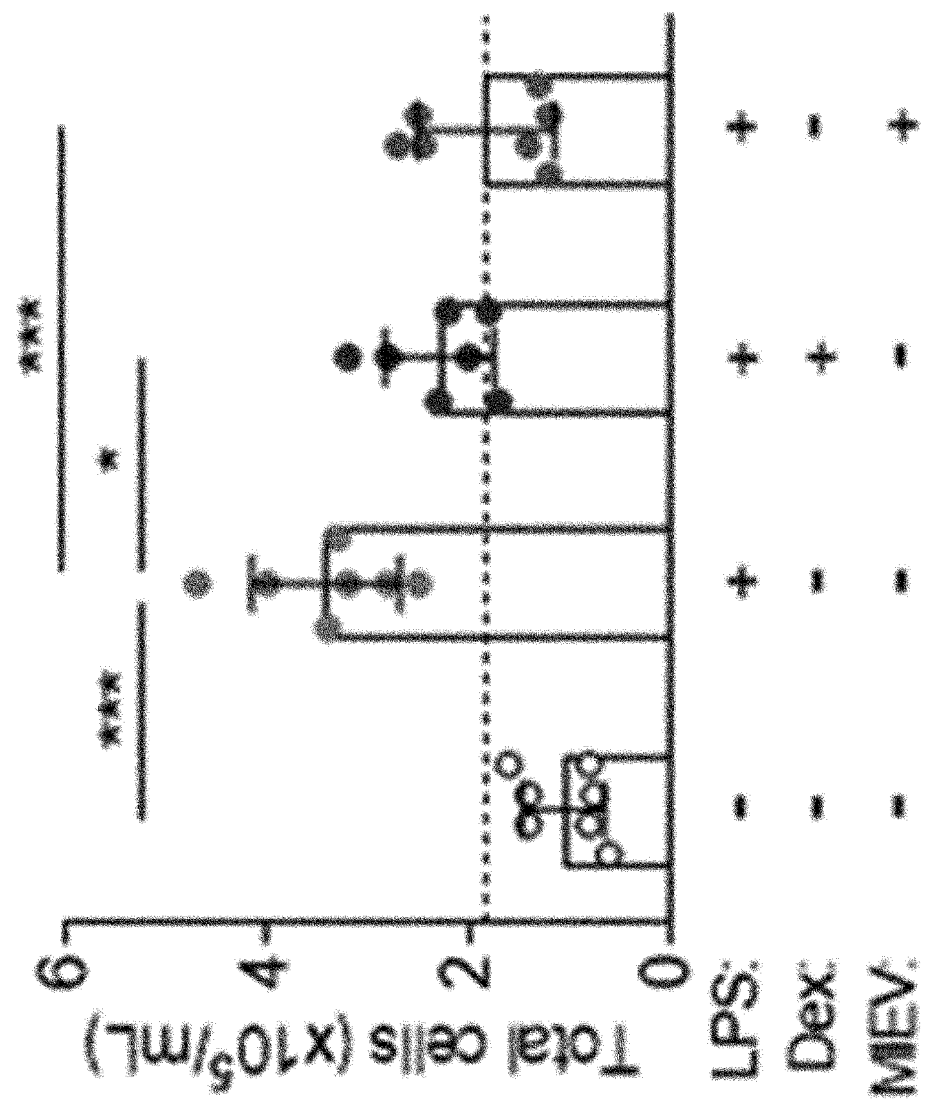
FIGS. 15A to 15C show an inflammation inhibitory effect of *Micrococcus luteus*-derived vesicles (*M. luteus* EVs) in mouse models with an immune disease caused by a protein contaminated by LPS.
Figure 15B:
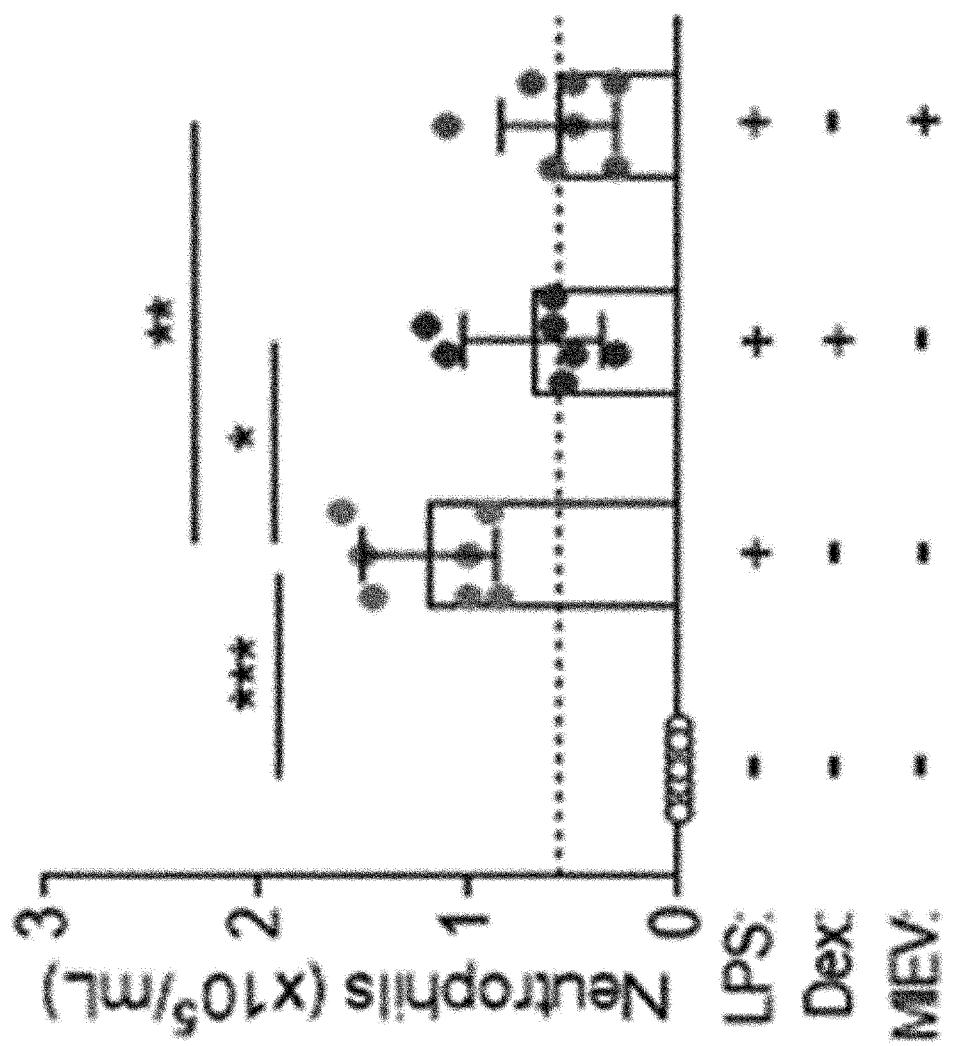

As a result, as shown in FIGS. 15A and 15B, similar to a group to which dexamethasone was administered, in a group to which vesicles derived from *Micrococcus luteus* were administered, it was confirmed that the total number of inflammatory cells (FIG. 15A) and the number of neutrophils (FIG. 15B) in bronchoalveolar lavage fluid (BALF) were significantly reduced.

Figure 15C:
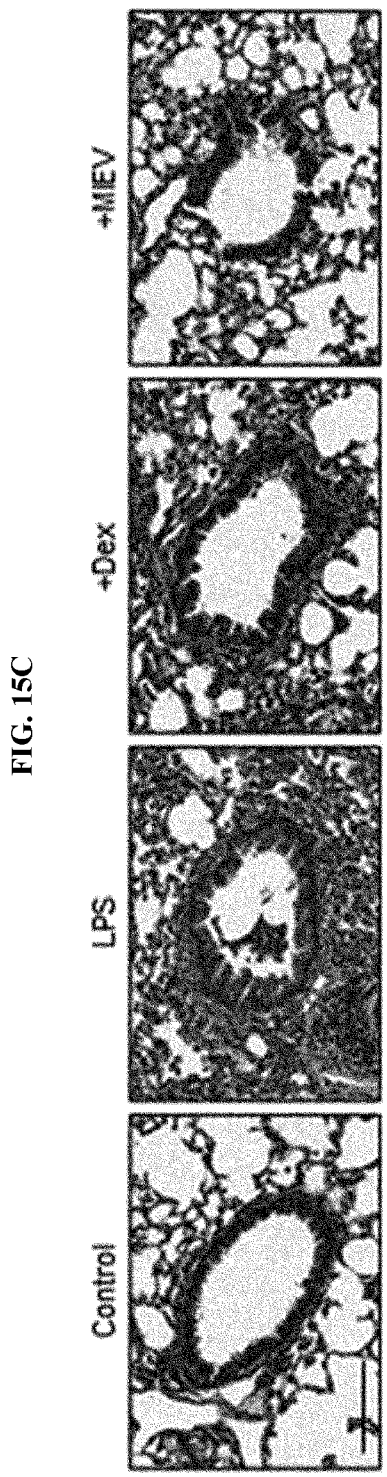

In addition, as shown in FIG. 15C, as a result of evaluating a histological change in the lung using Hematoxylin & Eosin staining, similar to a group to which dexamethasone was administered, in a group to which vesicles derived from *Micrococcus luteus* were administered, it was confirmed that the infiltration of inflammatory cells was significantly inhibited in lung tissue (FIG. 15C). From the result, it can be seen that an immune disease induced by PAMP can be efficiently treated by the vesicles derived from *Micrococcus luteus*.

Example 10. Confirmation of Immunological Mechanism of Action with Respect to Anti-Inflammatory Effect of Vesicles Derived from *Micrococcus luteus* in Mouse Model with Immune Disease Caused by Protein Contaminated by LPS To confirm an immunological mechanism of action with respect to an anti-inflammatory effect of vesicles derived from *Micrococcus luteus* using the mouse model of Example 9, IL-1β and IL-17 in bronchoalveolar lavage fluid (BALF) were measured using ELISA (R&D Systems).

Figure 16A:
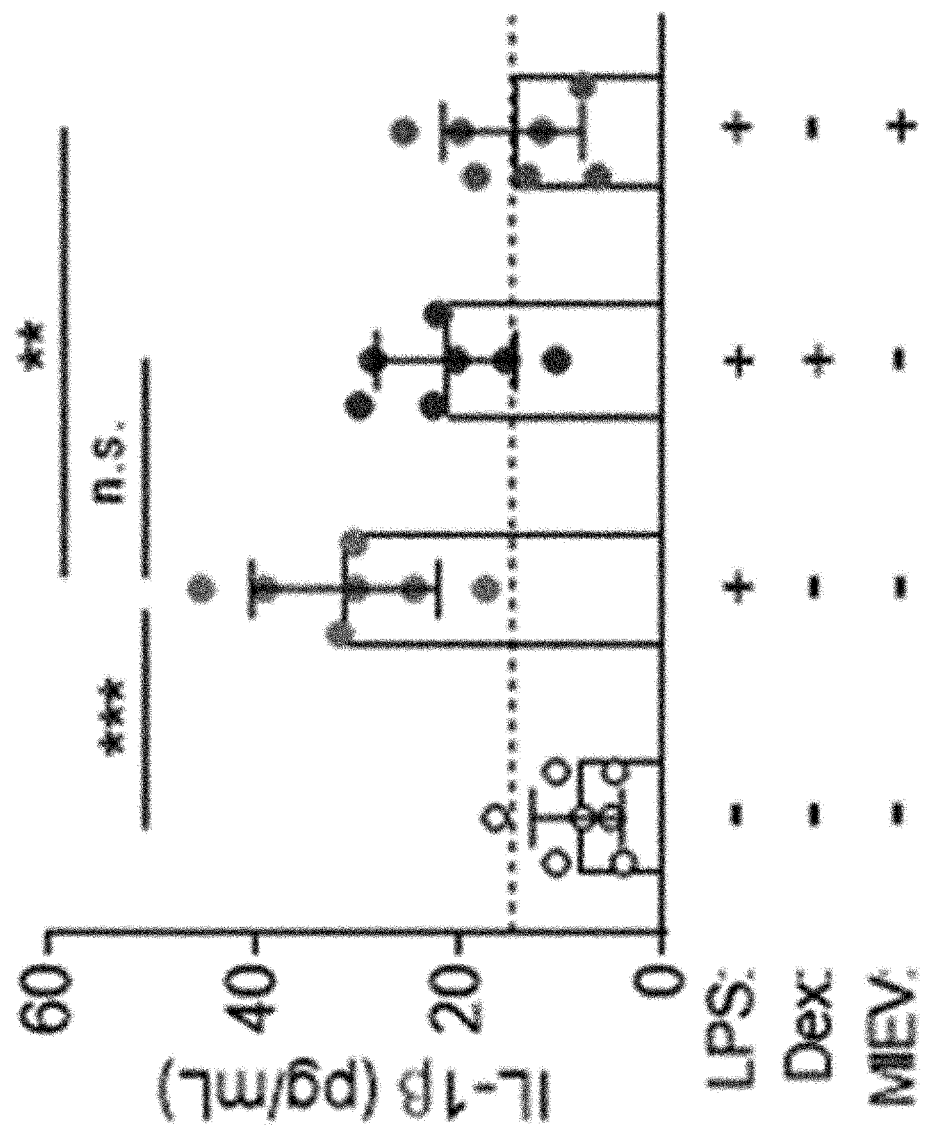
FIGS. 16A and 16B show effects of *Micrococcus luteus*-derived vesicles (*M. luteus* EVs) on IL-1$\beta$ and IL-17, which is a Th17 immune response indicator, in mouse models with an immune disease caused by a protein contaminated by LPS.
Figure 16B:
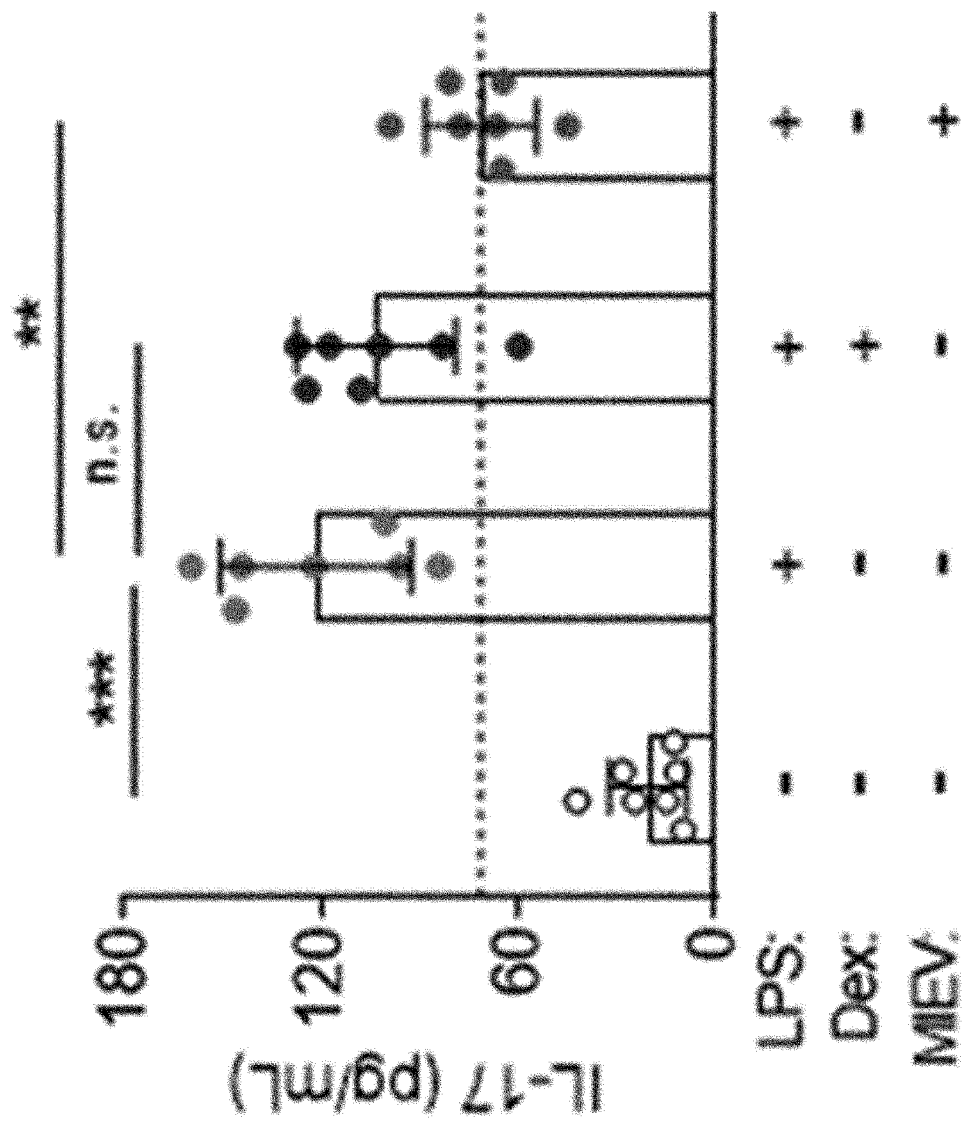

As a result, as shown in FIGS. 16A and 16B, it was confirmed that concentrations of an inflammatory cytokine such as IL-1β in the bronchoalveolar lavage fluid (BALF) (FIG. 16A) and an indicator for a Th17 immune response by PAMP, such as IL-17 (FIG. 16B) are significantly reduced by the vesicles derived from *Micrococcus luteus*. From the above result, it can be seen that the vesicles derived from *Micrococcus luteus* can treat a disease induced by PAMP by efficiently inhibiting a Th17 immune response by LPS.

Example 11. Confirmation of Molecular Biological Mechanism of Action of Vesicles Derived from *Micrococcus luteus* in Mouse Model with Immune Disease Caused by Protein Contaminated by LPS on Regulation of Immune Function It is known that the innate immune response to various stresses is very important in the pathogenesis of a disease. Particularly, an NLRP3 protein present in the cytoplasm is known as a critical signaling pathway in the pathogenesis of an age-related ocular disease and an inflammatory ocular disease. In addition, t-bet and ROR-γt associated with the development of an acquired immune response to an antigen are known as key signaling materials related to the differentiation of Th1 and Th17 immune cells against antigens, respectively.

To evaluate the molecular biological action mechanism to the regulation of immune function of the vesicles derived from *Micrococcus luteus*, the expression of NOD-like receptor pyrin domain-containing protein 3 (NLRP3), a t-box protein expressed in T cells (t-bet) and retinoic-acid-receptor-related orphan nuclear receptor gamma (ROR-γt) in lung tissue of the mouse model of Example 9 was confirmed by western blotting. Specifically, to measure an expression level of each protein, 50 µg of the protein was used, and in lung tissue of a mouse group to which dexamethasone (Dex) or vesicles derived from *Micrococcus luteus* were administered, protein expression was confirmed.

Figure 17:
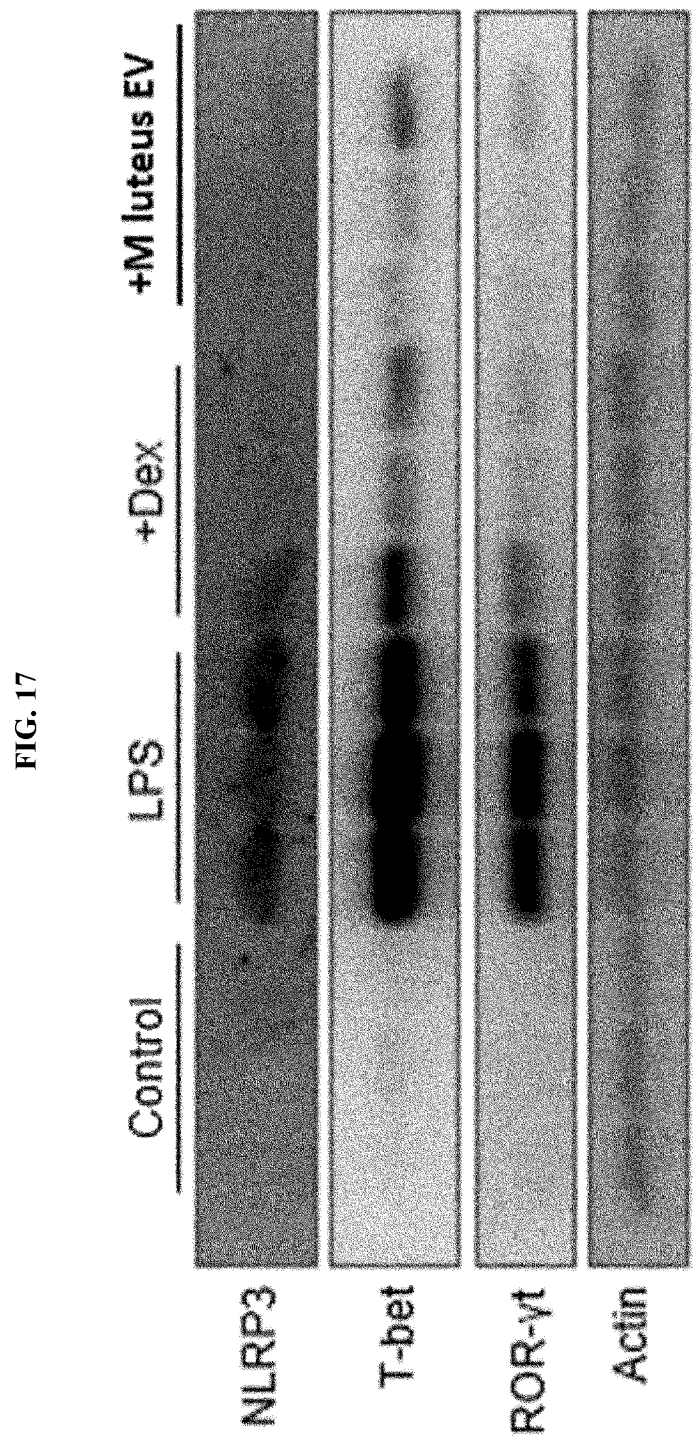
FIG. 17 is a result of confirming expression patterns of immune function-regulating proteins, such as NLRP3, T-bet and ROR-rt in lung tissue isolated from mouse models with an immune disease caused by a protein contaminated by LPS in order to evaluate a mechanism of regulating immune function by *Micrococcus luteus*-derived vesicles (*M. luteus* EVs).

As a result, as shown in FIG. 17, it was confirmed that, compared to a negative control, in a group to which a protein contaminated by LPS was administered, NLRP3 expression was significantly increased, and in lung tissue of group to which vesicles derived from *Micrococcus luteus* were administered, similar to a group to which dexamethasone was administered, the expression of NLRP3, t-bet and ROR-γt is significantly inhibited.

NLRP3 is a key pattern-recognition receptor (PRR) secreting IL-1β by expressing monocytes and macrophages in bacterial and viral infection. From the above result, it can be seen that the vesicles derived from *Micrococcus luteus* inhibited NLRP3 expression to regulate innate immune function. In addition, t-bet and ROR-γt, which are associated with the development of an acquired immune response to antigens, are key signaling materials related to the differentiation of Th1 and Th17 immune cells against antigens, respectively. From the above result, it can be seen that the vesicles derived from *Micrococcus luteus* inhibit the differentiation into and activation of Th17 immune cells secreting Th1 and IL-17 by inhibiting t-bet and ROR-γt expression.

This means that abnormal immune function induced by PAMP such as LPS is efficiently inhibited by the vesicles derived from *Micrococcus luteus*.

Example 12. Evaluation of Efficacy of Vesicles Derived from *Micrococcus luteus* in Regulation of Cell Homeostasis by Oxidative Stress When cells are repeatedly exposed to various types of stress, cell senescence occurs due to oxidative stress in cells, abnormal cell functions occur, and cell death is caused, leading to a degenerative disease caused by aging. Particularly, a low concentration of nitric oxide (NO) produced through eNOS signaling plays a critical role in maintaining cell homeostasis by antagonizing the action of reactive oxygen species (ROS), which is the main cause of oxidative stress. On the other hand, a high concentration of NO produced through iNOS signaling rather causes excessive stress on cells, causing abnormalities in immune and metabolic functions and thus promoting the occurrence of a disease.

To evaluation the effect of vesicles derived from *Micrococcus luteus* on cell homeostasis by oxidative stress, A549 cells were treated with the vesicles derived from *Micrococcus luteus* (*M. luteus* EVs) by the method disclosed in Example 3, and then an expression pattern of cell signaling was evaluated. As a specific method for evaluating the expression of a signaling protein, cells were lysed using a lysis buffer to extract a protein, followed by quantifying the protein using a BCA protein assay kit (Thermo, USA). 50 µg of the protein per sample was subjected to electrophoresis in a 10% polyacrylamide gel, and the isolated protein was transferred to a nitrocellulose membrane. After blocking with skim milk-added Tris-buffered saline (0.05% Tween 20; TBST) at room temperature for 30 minutes, a1/1,000 dilution of primary antibodies specific for p-ERK, ERK, p-p38, p38, p-JNK, JNK, p-p65, p65, iNOS, p-eNOS, eNOS and β-actin was reacted at 4° C. for 24 hours. Subsequently, the resulting product was washed three times with PBST (0.05% Tween-20-containing phosphate buffer saline) for 10 minutes, and a 1/5,000 dilution of secondary antibodies was reacted at room temperature for 1 hour. After washing with PBST five times for 10 minutes, bands were detected using an ECL select reagent.

Figure 18A:
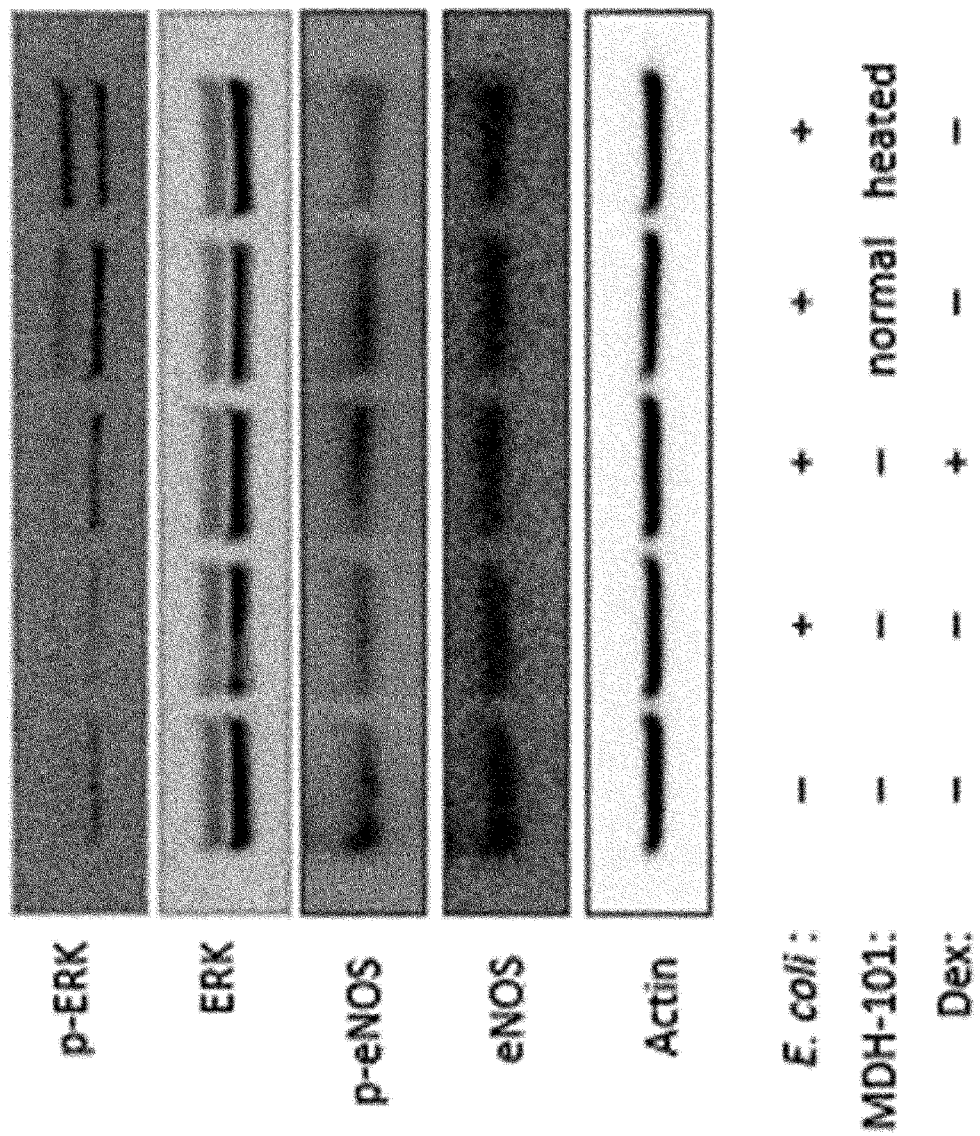
FIGS. 18A and 18B show eNOS signaling activity and iNOS signaling activity by *E. coli*-derived vesicles (*E. coli* EVs), which are virus-mimicking nanoparticles, by treating epithelial cells with *Micrococcus luteus*-derived vesicles and a positive control drug, dexamethasone, in order to evaluate a molecular biological mechanism of producing NO by *Micrococcus luteus*-derived vesicles (*M. luteus* EVs)

As a result, as shown in FIG. 18A, when vesicles derived from *Micrococcus luteus* were treated, ERK and eNOS phosphorylation were increased by dexamethasone (Dex) and the vesicles derived from *Micrococcus luteus* (*M. luteus* EVs). In addition, eNOS signaling by the vesicles derived from *Micrococcus luteus* was inhibited by heat treatment on the vesicles derived from *Micrococcus luteus*. The above result can show that the vesicles derived from *Micrococcus luteus* activate eNOS signaling to induce a low concentration of NO in cells and increase cell homeostasis, and the effects of producing a low concentration of NO and inhibiting oxidative stress through the eNOS signaling are mediated by a heat-vulnerable protein in the vesicles.

Figure 18B:
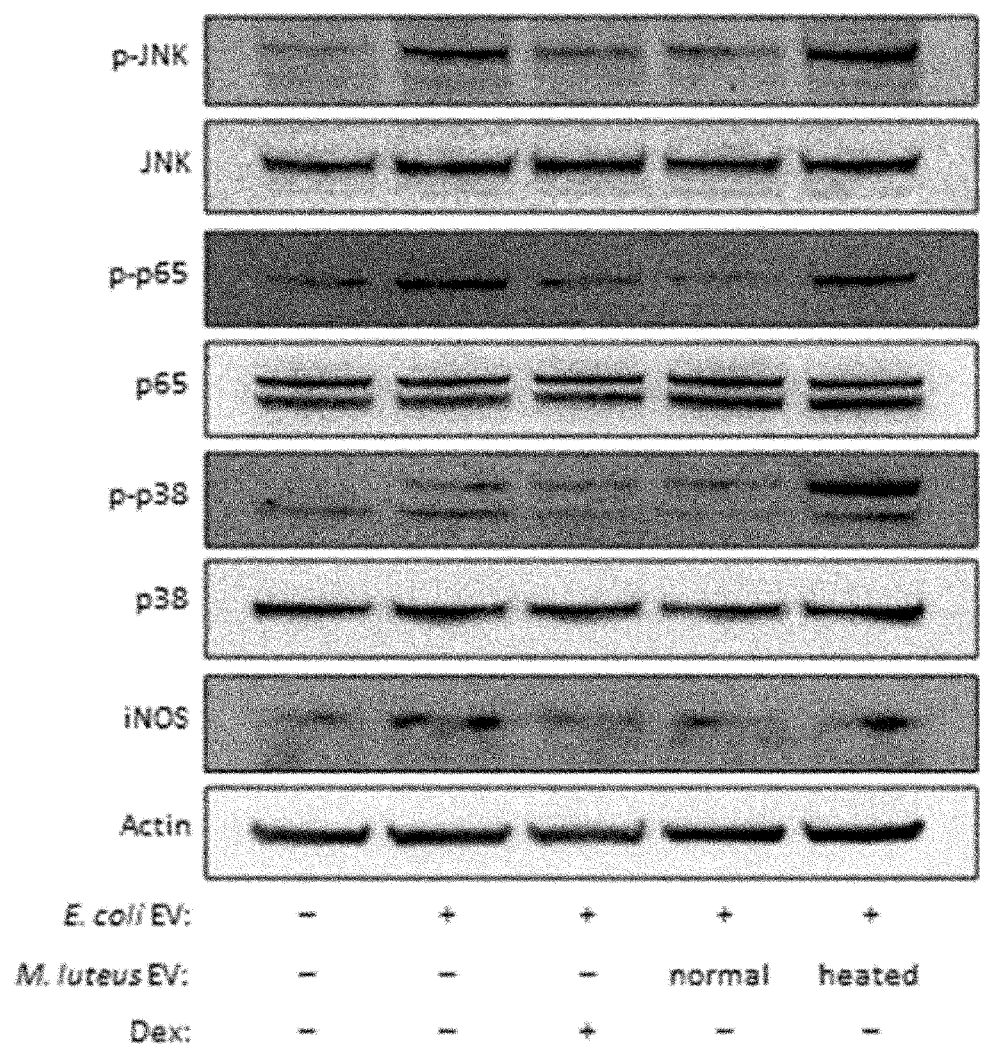

On the other hand, as shown in FIG. 18B, when the vesicles derived from *Micrococcus luteus* were treated, JNK, p65 and p38 phosphorylation and iNOS expression were inhibited. In addition, the iNOS expression indicates that, even when membrane protein function was inhibited by heat treatment on the vesicles derived from *Micrococcus luteus*, the inhibitory effect of the vesicles was maintained. The above result can show that the production of a high concentration of NO through iNOS signaling and inflammation caused thereby are mediated by components other than a protein in the vesicles.

Figure 19:
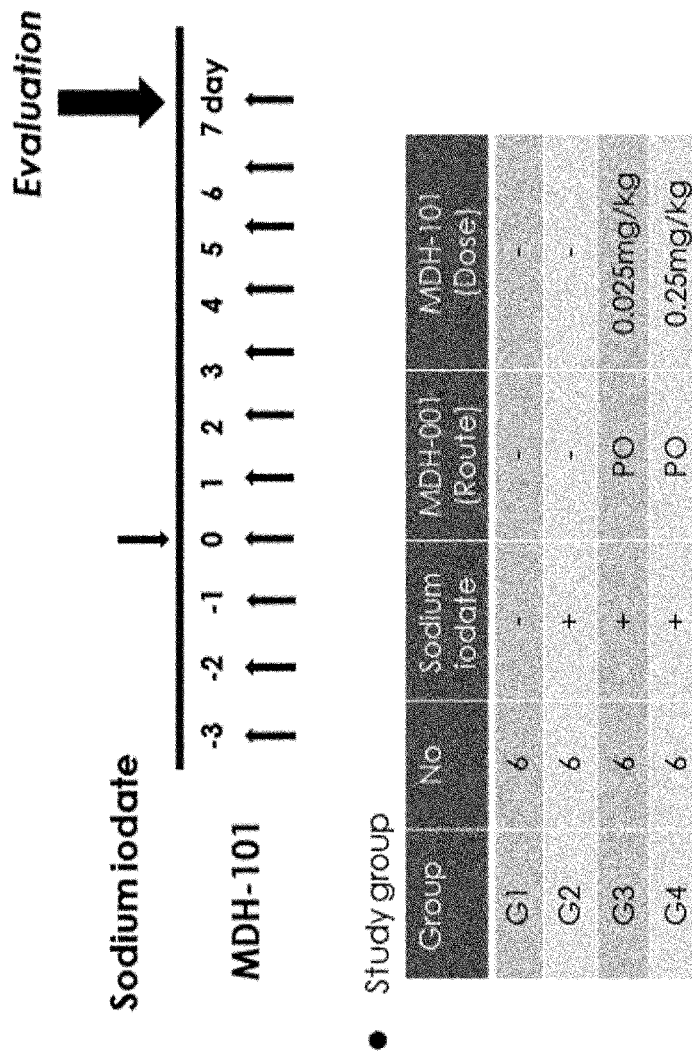
FIG. 19 shows an animal model experimental method and its evaluation method for evaluating an effect of *Micrococcus luteus*-derived vesicles (*M. luteus* EVs) on an ocular disease.

Example 13: Evaluation of Therapeutic Effect of Vesicles Derived from *Micrococcus luteus* in Rabbit Model with Ocular Disease Caused by Oxidative Stress To induce an ocular disease, sodium iodate (SI), which is a material for inducing retinal degeneration by oxidative stress, was intravenously administered into a rabbit once. More specifically, as shown in FIG. 19, to evaluate the therapeutic effect of the vesicles derived from *Micrococcus luteus*, 0.025 mg/kg and 0.25 mg/kg of the vesicles derived from *Micrococcus luteus* (*M luteus* EVs) were orally administered once daily 3 days before induction to 7 days after induction. For evaluation, a retinal degenerated area was taken with a fundus camera (TRC-50IX, TOPCON, Japan) on the final administration day, i.e., on day 7 after induction of the disease, and analyzed.

Figure 20:
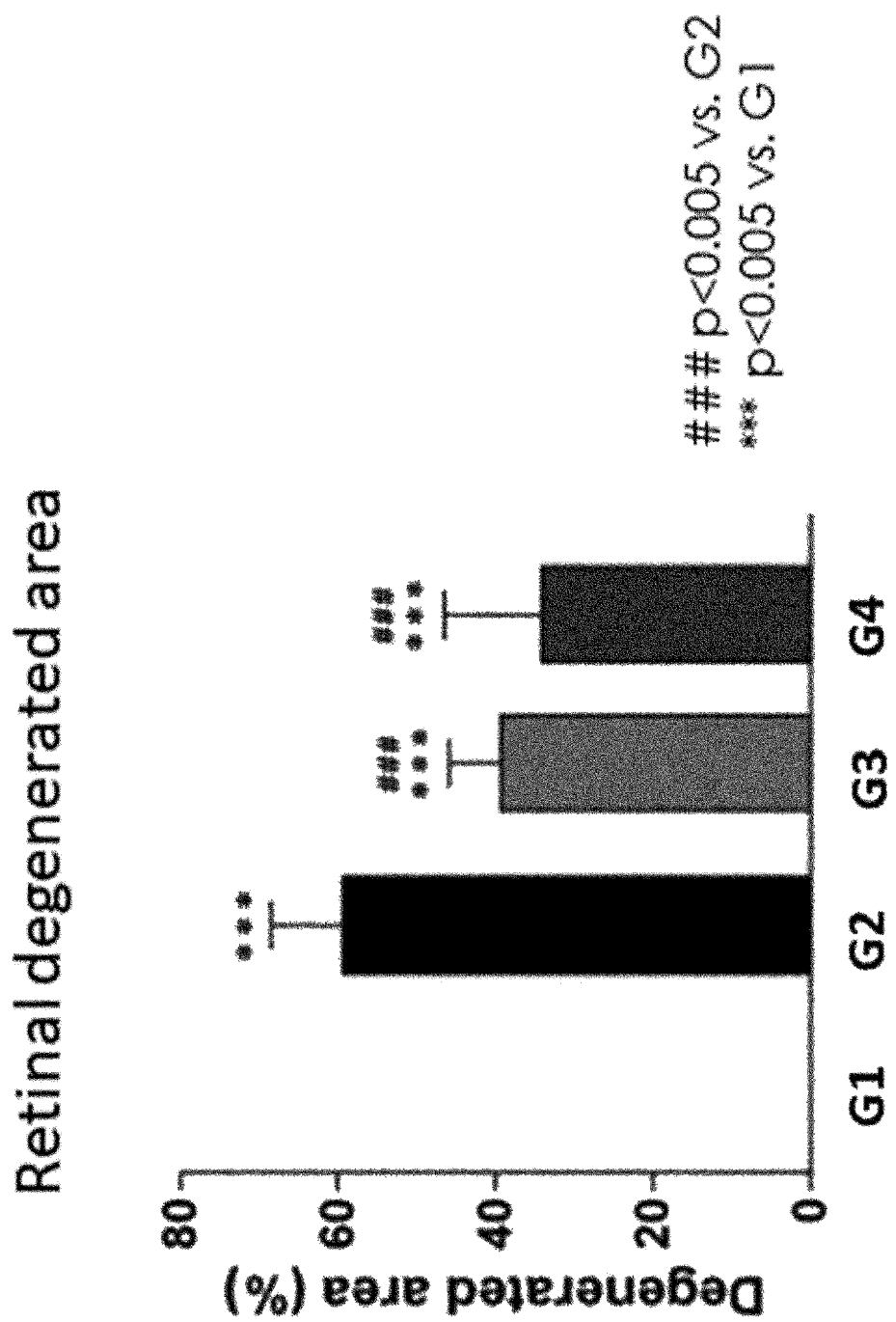
FIG. 20 shows a result obtained by measuring a retinal degenerated area of a *Micrococcus luteus*-derived vesicle-treated group compared to a control by orally administering *Micrococcus luteus*-derived vesicles (*M. luteus* EVs) into a rabbit model of an ocular disease caused by oxidative stress in order to evaluate an effect of the vesicles on an ocular disease.

As a result, as shown in FIG. 20, in a low-dose vesicle-treated group (G3) and a high-dose vesicle-treated group (G4), compared to a positive control (G2), the degenerated area of retina was statistically significantly reduced, confirming dose-dependence.

Meanwhile, to evaluate the effect of the vesicles derived from *Micrococcus luteus* in treatment of ocular disease, after instilling a mydriatic agent (Midriacil 1% eye drop) into the right eye of the rabbit, the animal was anesthetized, and then its fundus was photographed with a fundus camera. The result is shown in FIG. 21.

Figure 21:
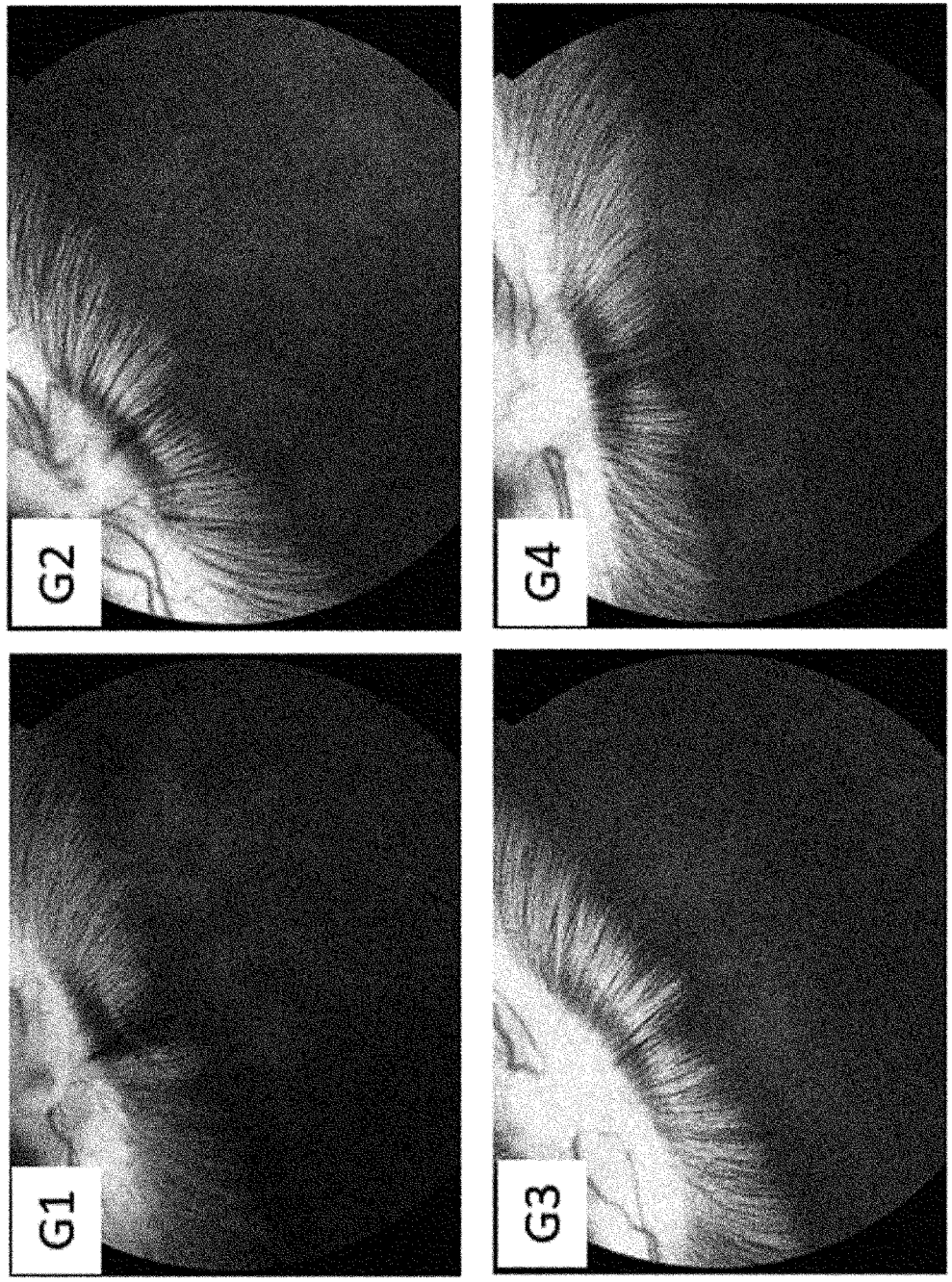
FIG. 21 is a set of photographs obtained by photographing the fungus with a fundus camera (TRC-50IX, TOPCON, Japan) after the vesicles are orally administered to a rabbit model with an ocular disease caused by oxidative stress.

As shown in FIG. 21, it can be seen that, in the positive control (G2), compared to the negative control (G1), retinal degeneration significantly increases, and in the low-dose vesicle-treated group (G3) and high-dose vesicle-treated group (G4), compared to the positive control, retinal degeneration is significantly reduced.

Figure 22:
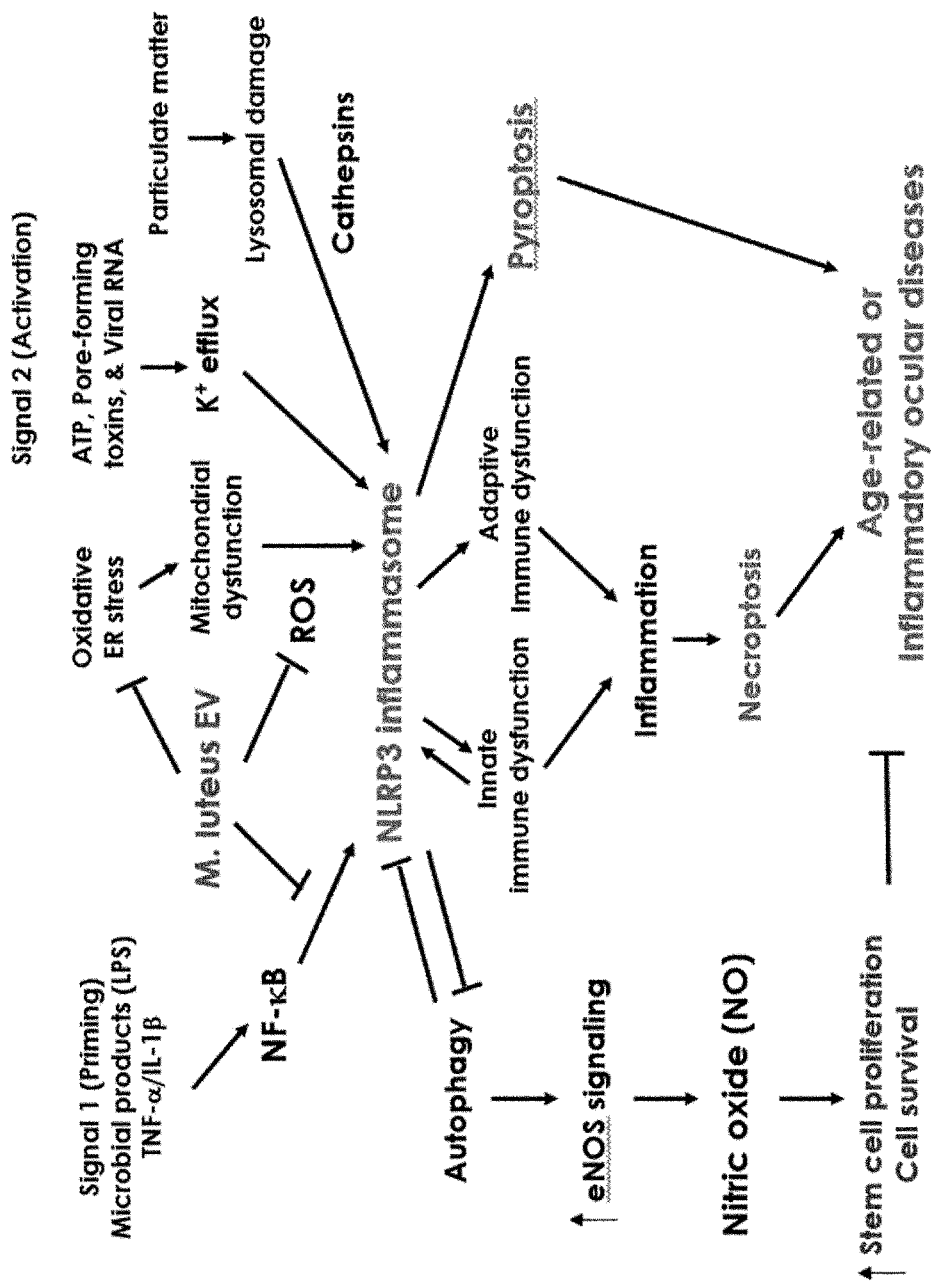
FIG. 22 is a diagram illustrating a mechanism of action of *Micrococcus luteus*-derived vesicles (*M. luteus* EVs) on an ocular disease.

The above result can show that the vesicles derived from *Micrococcus luteus* of the present invention efficiently inhibited an ocular disease occurring due to aging or inflammation. Particularly, it can be seen that the vesicles derived from *Micrococcus luteus* restore innate immune and acquired immune functions by inhibiting NLRP3 inflammasome signaling induced by oxidative stress, abnormal mitochondrial function and lysosomal damage. In addition, it can be seen that the eNOS signaling induces low-concentration NO production to increase cell homeostasis. Particularly, when the vesicles derived from *Micrococcus luteus* are orally administered, they are dispersed in the central nervous system through the blood-brain barrier (BBB), confirming that, as shown in FIG. 22, cell death due to abnormal immune function of vision-related nerve cells is inhibited, and cell homeostasis is efficiently increased. Therefore, it is expected that the vesicles derived from *Micrococcus luteus* of the present invention can be used for alleviating, preventing or treating an age-related ocular disease and an inflammatory ocular disease.

Example 14. Evaluation of Effect of Vesicles Derived from *Micrococcus luteus* in Mouse Model with Inflammatory Disease Caused by Pathogenic Nanoparticles As a result of confirming the effect of vesicles derived from bacteria of the genus *Micrococcus* in a mouse model with an inflammatory disease caused by pathogenic nanoparticles as shown in Example 6, in a group to which the vesicles derived from bacteria of the genus *Micrococcus* are treated, it can be confirmed that the extracellular vesicles are effective in treating intractable diseases, for example, respiratory diseases such as asthma and pneumonia; liver diseases such as hepatitis, cirrhosis, and liver cancer; kidney diseases such as glomerulonephritis and diabetic nephropathy; and/or brain diseases such as Alzheimer's disease, Parkinson's disease and Lou Gehrig's disease in a dose-dependent manner.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The inventors confirmed that, when vesicles derived from *Micrococcus luteus* were orally administered, the extracellular vesicles were delivered to the central nervous system through the blood brain barrier (BBB). In addition, it was confirmed that, when epithelial cells and macrophages were treated with the extracellular vesicles, not only is the secretion of an inflammatory mediator by a biological causative factor considerably inhibited, but also NLRP3 protein expression by a biological causative factor is inhibited. Further, it was confirmed that, when the extracellular vesicles are administered to a rabbit model with an ocular disease caused by oxidative stress, retinal degeneration caused by oxidative stress is significantly inhibited. Thus, it is expected that the vesicles derived from *Micrococcus luteus* according to the present invention can be effectively used for not only a composition for preventing, alleviating or treating an ocular disease, but also a drug delivery system for treating an ocular disease.

The invention claimed is:

1. A method for alleviating or treating an ocular disease, the method comprising administering a composition consisting of vesicles derived from *Micrococcus luteus* as an active ingredient, and a pharmaceutically acceptable carrier or food ingredient, to a subject in need thereof, wherein the ocular disease is mediated by an NOD-like receptor pyrin domain-containing protein 3 (NLRP3) inflammasome.

2. The method of claim 1, wherein the ocular disease is an age-related ocular disease.

3. The method of claim 2, wherein the ocular disease is one or more diseases selected from the group consisting of retinal geographic atrophy, diabetic retinopathy, cataracts, glaucoma, and xerophthalmia.

4. The method of claim 1, wherein the ocular disease is an inflammatory ocular disease.

5. The method of claim 4, wherein the ocular disease is one or more diseases selected from the group consisting of conjunctivitis, scleritis, keratitis, iritis, uveitis, chorioretinitis, choroiditis, and retinitis.

6. The method of claim 1, wherein the vesicles have an average diameter of 10 to 200 nm.

7. The method of claim 1, wherein the vesicles are naturally secreted or artificially produced from *Micrococcus luteus*.

8. The method of claim 1, wherein the composition inhibits the activity of an NOD-like receptor pyrin domain-containing protein 3 (NLRP3) inflammasome.

9. The method of claim 1, wherein the composition is a pharmaceutical composition.

10. The method of claim 1, wherein the composition is a food composition.

11. The method of claim 1, wherein the composition is a quasi-drug composition.

12. The method of claim 1, wherein the composition is an inhalant composition.

13. A method of delivering a drug for treating an ocular disease, the method comprising administering a composition comprising vesicles derived from *Micrococcus luteus* and containing a target drug for treating an ocular disease as an active ingredient to a subject in need thereof.

14. The method of claim 1, wherein the composition is administered via oral administration.

15. The method of claim 1, wherein the ocular disease is a retinal degeneration caused by oxidative stress.

* * * * *